United States Patent
Flitsch et al.

(10) Patent No.: US 10,413,182 B2
(45) Date of Patent: Sep. 17, 2019

(54) BIOMEDICAL DEVICES FOR BIOMETRIC BASED INFORMATION COMMUNICATION

(71) Applicant: Johnson & Johnson Vision Care, Inc., Jacksonville, FL (US)

(72) Inventors: Frederick A. Flitsch, New Windsor, NY (US); Jorge Gonzalez, Washington, DC (US); Randall B. Pugh, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 9 days.

(21) Appl. No.: 14/994,390

(22) Filed: Jan. 13, 2016

(65) Prior Publication Data
US 2017/0020390 A1 Jan. 26, 2017

Related U.S. Application Data

(60) Provisional application No. 62/196,513, filed on Jul. 24, 2015.

(51) Int. Cl.
*A61B 5/00* (2006.01)
*A61B 5/01* (2006.01)
(Continued)

(52) U.S. Cl.
CPC ............ *A61B 5/0002* (2013.01); *A61B 3/112* (2013.01); *A61B 3/113* (2013.01); *A61B 3/16* (2013.01); *A61B 5/0022* (2013.01); *A61B 5/01* (2013.01); *A61B 5/021* (2013.01); *A61B 5/024* (2013.01); *A61B 5/1103* (2013.01);
(Continued)

(58) Field of Classification Search
CPC combination set(s) only.
See application file for complete search history.

(56) References Cited

U.S. PATENT DOCUMENTS 5,359,669 A   10/1994   Shanley et al.
6,458,080 B1  10/2002   Brown
(Continued)

FOREIGN PATENT DOCUMENTS

CN   102184312 A   9/2011
EP      942278 A2   9/1999
(Continued)

OTHER PUBLICATIONS

Ghafar-Zadeh, Ebrahim, "Wireless Integrated Biosensors for Point-of Care Diagnostic Applications", Sensors 2015, 15, 3236-3261.
(Continued)

*Primary Examiner* — Brian A Zimmerman
*Assistant Examiner* — Cal J Eustaquio

(57) ABSTRACT

Methods and apparatus to form a biometric based information communication system are described. In some examples, the biometric based information communication system comprises biomedical devices with sensing means, wherein the sensing means produces a biometric result. In some examples the biometric based information communication system may comprise a user device such as a smart phone paired in communication with the biomedical device. A biometric measurement result may trigger a communication of a biometric based information communication message.

8 Claims, 20 Drawing Sheets

(51) Int. Cl.

| | | |
|---|---|---|
| *A61B 5/021* | (2006.01) | |
| *A61B 5/024* | (2006.01) | |
| *A61B 5/11* | (2006.01) | |
| *A61B 5/145* | (2006.01) | |
| *A61B 3/11* | (2006.01) | |
| *A61B 3/113* | (2006.01) | |
| *A61B 3/16* | (2006.01) | |
| *G02C 7/04* | (2006.01) | |
| *G06Q 30/02* | (2012.01) | |
| *G16H 40/67* | (2018.01) | |
| *A61B 5/1455* | (2006.01) | |

(52) U.S. Cl.
CPC ........ *A61B 5/1112* (2013.01); *A61B 5/14532* (2013.01); *A61B 5/14542* (2013.01); *A61B 5/486* (2013.01); *A61B 5/681* (2013.01); *A61B 5/6802* (2013.01); *A61B 5/6803* (2013.01); *A61B 5/6821* (2013.01); *A61B 5/6898* (2013.01); *A61B 5/7271* (2013.01); *A61B 5/742* (2013.01); *A61B 5/7455* (2013.01); *G02C 7/04* (2013.01); *G06Q 30/0261* (2013.01); *G06Q 30/0267* (2013.01); *G06Q 30/0269* (2013.01); *G16H 40/67* (2018.01); *A61B 5/14546* (2013.01); *A61B 5/14551* (2013.01); *A61B 5/7275* (2013.01); *A61B 5/7405* (2013.01); *A61B 2560/0242* (2013.01)

(56) References Cited

U.S. PATENT DOCUMENTS

| | | | | |
|---|---|---|---|---|
| 7,620,212 | B1* | 11/2009 | Allen | G06K 9/0004 340/5.53 |
| 8,909,311 | B2 | 12/2014 | Ho et al. | |
| 9,810,910 | B1* | 11/2017 | Park | G02B 27/0172 |
| 2002/0026111 | A1 | 2/2002 | Ackerman | |
| 2002/0161770 | A1* | 10/2002 | Shapiro | G06F 17/211 |
| 2003/0004403 | A1 | 1/2003 | Drinan et al. | |
| 2003/0125017 | A1* | 7/2003 | Greene | A61B 5/0002 455/414.1 |
| 2004/0054291 | A1 | 3/2004 | Schulz et al. | |
| 2004/0073392 | A1* | 4/2004 | Immonen | G01S 5/021 702/89 |
| 2004/0190759 | A1 | 9/2004 | Caldwell | |
| 2004/0236199 | A1 | 11/2004 | Hawthorne | |
| 2004/0242976 | A1 | 12/2004 | Abreu | |
| 2004/0257196 | A1* | 12/2004 | Kotzin | G07C 9/00142 340/5.52 |
| 2005/0113650 | A1 | 5/2005 | Pacione | |
| 2005/0113654 | A1 | 5/2005 | Weber et al. | |
| 2005/0143617 | A1 | 6/2005 | Auphan | |
| 2005/0149170 | A1 | 7/2005 | Tassel et al. | |
| 2005/0175665 | A1 | 8/2005 | Hunter et al. | |
| 2006/0029264 | A1 | 2/2006 | Utsunomiya | |
| 2006/0150332 | A1 | 7/2006 | Weismiller et al. | |
| 2006/0189854 | A1 | 8/2006 | Webb et al. | |
| 2006/0228011 | A1* | 10/2006 | Everett | A61B 3/102 382/128 |
| 2007/0078315 | A1 | 4/2007 | Kling et al. | |
| 2007/0173705 | A1 | 7/2007 | Teller | |
| 2008/0021336 | A1 | 1/2008 | Dobak, III | |
| 2008/0052837 | A1 | 3/2008 | Blumberg et al. | |
| 2008/0146892 | A1 | 6/2008 | LeBoeuf | |
| 2008/0208009 | A1 | 8/2008 | Shklarski | |
| 2008/0228046 | A1 | 9/2008 | Futatsuyama | |
| 2008/0249867 | A1 | 10/2008 | Angell et al. | |
| 2009/0058660 | A1* | 3/2009 | Torch | A61B 3/0066 340/573.1 |
| 2009/0118590 | A1 | 5/2009 | Teller et al. | |
| 2009/0125333 | A1 | 5/2009 | Heywood et al. | |
| 2009/0149704 | A1 | 6/2009 | Mitsuhashi | |
| 2009/0326981 | A1* | 12/2009 | Karkanias | G06Q 10/10 705/3 |
| 2010/0001841 | A1 | 1/2010 | Cardullo | |
| 2010/0049006 | A1 | 2/2010 | Magar et al. | |
| 2010/0185711 | A1* | 7/2010 | Subramaniam | A61B 5/0002 340/286.07 |
| 2010/0214111 | A1* | 8/2010 | Schuler | H04W 4/02 340/686.1 |
| 2010/0268051 | A1 | 10/2010 | Prasad et al. | |
| 2011/0004076 | A1 | 1/2011 | Janna et al. | |
| 2011/0015504 | A1* | 1/2011 | Yoo | A61B 5/0002 600/301 |
| 2011/0084834 | A1 | 4/2011 | Sabeta | |
| 2011/0190594 | A1 | 8/2011 | Heit et al. | |
| 2012/0050046 | A1* | 3/2012 | Satorius | G06F 19/3418 340/573.1 |
| 2012/0129460 | A1* | 5/2012 | Hodis | G01S 19/48 455/67.11 |
| 2012/0138067 | A1 | 6/2012 | Rawls-Meehan | |
| 2012/0184825 | A1 | 7/2012 | Ben David | |
| 2012/0212345 | A1 | 8/2012 | Harman | |
| 2012/0277568 | A1 | 11/2012 | Chiou | |
| 2012/0313776 | A1 | 12/2012 | Utter, II | |
| 2013/0131465 | A1 | 5/2013 | Yamamoto et al. | |
| 2013/0155410 | A1 | 6/2013 | Enderby et al. | |
| 2013/0194540 | A1 | 8/2013 | Pugh | |
| 2013/0253286 | A1 | 9/2013 | Fridman | |
| 2013/0278396 | A1 | 10/2013 | Kimmel | |
| 2014/0055749 | A1 | 2/2014 | Zhou et al. | |
| 2014/0081154 | A1 | 3/2014 | Toth | |
| 2014/0107493 | A1* | 4/2014 | Yuen | H04W 4/027 600/473 |
| 2014/0114677 | A1 | 4/2014 | Holmes | |
| 2014/0139405 | A1 | 5/2014 | Ribble et al. | |
| 2014/0143551 | A1* | 5/2014 | Rothschild | G06F 21/602 713/189 |
| 2014/0180036 | A1 | 6/2014 | Bukkapatnam et al. | |
| 2014/0193045 | A1 | 7/2014 | Otis et al. | |
| 2014/0194706 | A1 | 7/2014 | Liu et al. | |
| 2014/0200421 | A1 | 7/2014 | Gilland | |
| 2014/0240124 | A1 | 8/2014 | Bychkov | |
| 2014/0240665 | A1 | 8/2014 | Pugh | |
| 2014/0247147 | A1 | 9/2014 | Proud | |
| 2014/0257058 | A1 | 9/2014 | Clarysse | |
| 2014/0276119 | A1 | 9/2014 | Venkatraman et al. | |
| 2014/0276239 | A1 | 9/2014 | Subramaniam et al. | |
| 2014/0320820 | A1* | 10/2014 | Kumarasamy | A61B 3/0008 351/221 |
| 2014/0340630 | A1 | 11/2014 | Pugh | |
| 2014/0340631 | A1 | 11/2014 | Pugh | |
| 2014/0355842 | A1 | 12/2014 | Otis et al. | |
| 2014/0378786 | A1 | 12/2014 | Hong | |
| 2015/0065905 | A1 | 3/2015 | Pugh | |
| 2015/0087249 | A1 | 3/2015 | Pugh et al. | |
| 2015/0141772 | A1 | 5/2015 | LeBoeuf | |
| 2015/0148648 | A1 | 5/2015 | Pugh | |
| 2015/0170504 | A1 | 6/2015 | Jooste et al. | |
| 2015/0173602 | A1 | 6/2015 | Barrows et al. | |
| 2015/0182113 | A1 | 7/2015 | Utter, II | |
| 2015/0182163 | A1 | 7/2015 | Utter | |
| 2015/0186702 | A1 | 7/2015 | Pletcher | |
| 2015/0241347 | A1 | 8/2015 | Emadi | |
| 2015/0367097 | A1 | 12/2015 | Gavish | |
| 2016/0078191 | A1* | 3/2016 | Casimiro | G06F 19/3418 705/3 |
| 2016/0121074 | A1 | 5/2016 | Ashby | |
| 2016/0150582 | A1* | 5/2016 | Jung | H04W 12/04 455/41.1 |
| 2016/0217672 | A1 | 7/2016 | Yoon et al. | |
| 2017/0100064 | A1 | 4/2017 | Van Dorpe et al. | |

FOREIGN PATENT DOCUMENTS

| | | |
|---|---|---|
| EP | 1072994 A2 | 1/2001 |
| EP | 1434164 A2 | 6/2004 |
| EP | 1645255 A1 | 4/2006 |
| EP | 2732761 A1 | 5/2014 |
| EP | 2876489 A1 | 5/2015 |
| EP | 3106085 A1 | 12/2016 |
| JP | 2007275490 A | 10/2007 |

(56) References Cited

FOREIGN PATENT DOCUMENTS

| KR | 2014134785 A | 11/2014 |
|---|---|---|
| WO | WO1996039977 A1 | 12/1996 |
| WO | WO2010124275 A1 | 10/2010 |
| WO | WO2014186368 A1 | 11/2014 |
| WO | WO-2015082564 A1 | 6/2015 |
| WO | WO2015157855 A1 | 10/2015 |

OTHER PUBLICATIONS

Anliker et al., AMON: A Wearable Multiparameter Medical Monitoring and Alert System. IEEE Transactions on information technology in biomedicine, Dec. 4, 2004, vol. 8, No. 4, pp. 415-427.
D8—Guardian® REAL-Time continuous glucose monitoring system. Sep. 12, 2012 p. 40, 63: https://www.medtronicdiabetes.com/download-library/guardian-real-time.
Ford Wants Your Next Car to Monitor Your Vital Signs as You Drive. May 19, 2011: https://web.archive.org/web/20110522155731/http://www.popsci.com/cars/article/2011-05/how-new-apps-could-make-your-car-your-most-trustedpersonal-assistant.
Singapore Written Opinion date of completion Sep. 1, 2018 for Application: 10201606064Q.
Singapore Written Opinion date of completion Dec. 12, 2017 for Application: 10201606062Y.
Singapore Written Opinion date of completion Dec. 6, 2017 for Application: 10201606067X.
Singapore Written Opinion date of completion Dec. 28, 2017 for Application: 10201606069S.
Singapore Written Opinion date of completion Feb. 2, 2018 for Application: 10201606072U.
Singapore Written Opinion date of completion Mar. 3, 2018 for Application: 10201606073P.
Singapore Written Opinion date of completion Dec. 28, 2017 for Application: 10201606074Y.
Singapore Written Opinion date of completion Jul. 21, 2017 for Application: 10201606076S.
Singapore Written Opinion date of completion Jul. 21, 2017 for Application: 10201606081V.
Singapore Written Opinion date of completion Dec. 15, 2017 for Application: 10201606079V.
Extended European Search Report for Application No. 16180937.1, dated Dec. 21, 2016, 8 pages.
Extended European Search Report for Application No. 16180965.2, dated Mar. 23, 2017, 16 pages.
Extended European Search Report for Application No. 16181008.0, dated Dec. 21, 2016, 10 pages.
Extended European Search Report for Application No. 16181079.1, dated Dec. 21, 2016, 9 pages.
Extended European Search Report for Application No. 16181080.9, dated Dec. 21, 2016, 8 pages.
Extended European Search Report for Application No. 16181084.1, dated Dec. 21, 2016, 8 pages.
Extended European Search Report for Application No. 16181086.6, dated Dec. 22, 2016, 8 pages.
Extended European Search Report for Application No. 16181089.0, dated Mar. 14, 2017, 16 pages.
Extended European Search Report for Application No. 16181091.6, dated Dec. 21, 2016, 10 pages.
Extended European Search Report for Application No. 16181096.5, dated Dec. 21, 2016, 8 pages.
Kazunori Hoshino., et al., "Use of Colloidal Quantum Dots as a Digitally Switched Swept Light Source for Gold Nanoparticle Based Hyperspectral Microscopy," Biomedical Optics Express, Apr. 2014, pp. 1610-1615.
Krstajic N., et al., "Optical Coherence Tomography with High Power Quantum-dot Superluminescent Diodes," IEEE LEOS Annual Meeting Conference Proceedings, Oct. 2009, pp. 207-208.
Partial European Search Report for Application No. 16180965.2, dated Dec. 23, 2016, 9 pages.
Partial European Search Report for Application No. 16181089.0, dated Dec. 23, 2016, 9 pages.
Bao J., et al., "A Colloidal Quantum Dot Spectrometer", Nature, Jul. 1, 2015, vol. 523(7558), pp. 67-70.
International Search Report and Written Opinion for Application No. PCT/IB2018/050129, dated Apr. 19, 2018, 18 pages.

\* cited by examiner

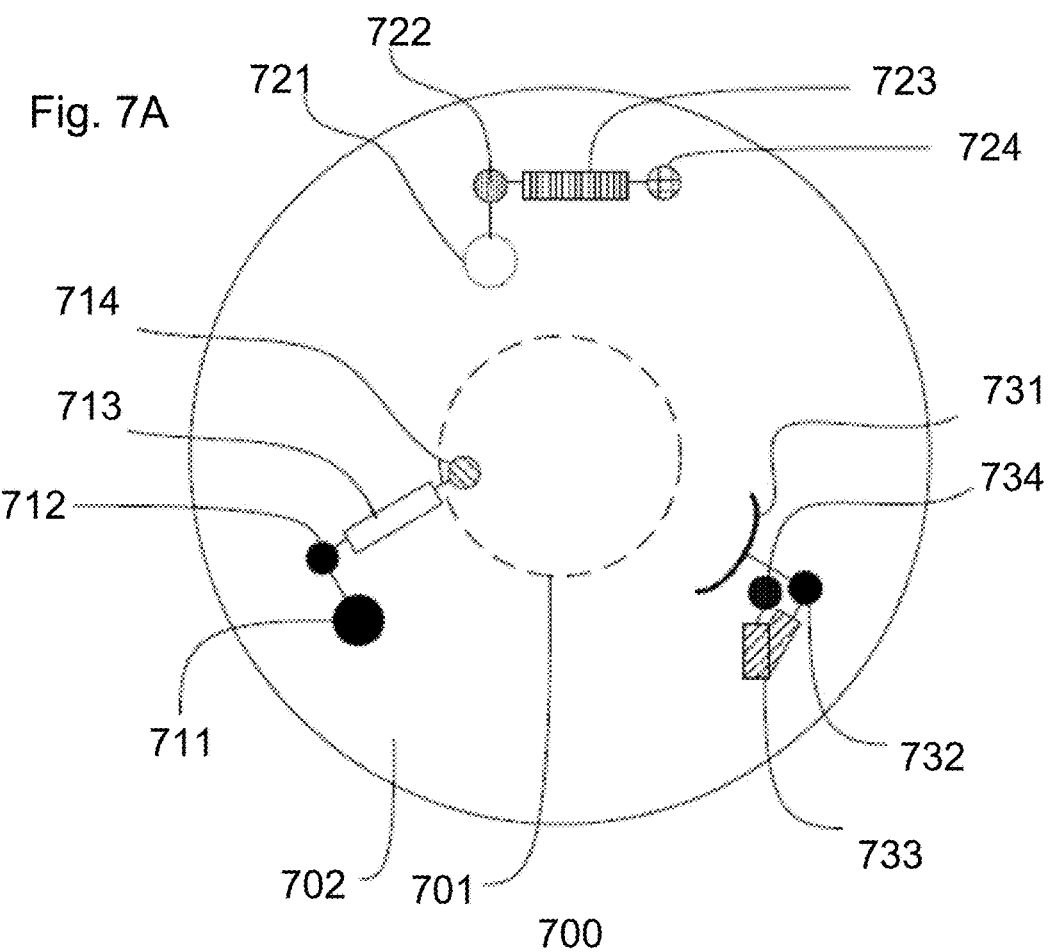
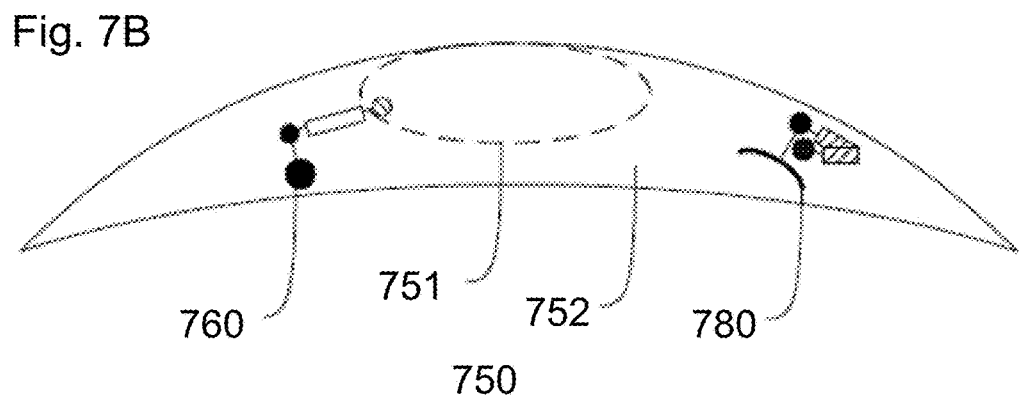

Exemplary Sensing of a Powered Biomedical Device

BIOMEDICAL DEVICES FOR BIOMETRIC BASED INFORMATION COMMUNICATION

CROSS REFERENCE TO RELATED APPLICATIONS

This patent application claims the benefit of U.S. Provisional Application No. 62/196,513 filed Jul. 24, 2015.

BACKGROUND OF THE INVENTION

1. Field of the Invention

Biomedical devices for information communication and GPS based information display are described. In some exemplary embodiments, the devices' functionality involves collecting biometric information along with GPS information to perform personalized information communication for the user of the device.

2. Discussion of the Related Art

Recently, the number of medical devices and their functionality has begun to rapidly develop. These medical devices may include, for example, implantable pacemakers, electronic pills for monitoring and/or testing a biological function, surgical devices with active components, contact lenses, infusion pumps, and neurostimulators. These devices are often exposed to and interact with biological and chemical systems making the devices optimal tools for collecting, storing, and distributing biometric data.

Some medical devices may include components such as semiconductor devices that perform a variety of functions including GPS positioning and biometrics collection, and may be incorporated into many biocompatible and/or implantable devices. However, such semiconductor components require energy and, thus, energization elements must also be included in such biocompatible devices. The addition of self-contained energy in a biomedical device capable of collecting biometrics and GPS positioning would enable the device to perform personalized information communication for the user of the device.

SUMMARY OF THE INVENTION

Accordingly, apparatus and methods for biometric based information display are discussed herein. The ability to measure biometric data and communicate the results in real time with sophisticated communication systems opens up new embodiments for the use of the biometric data. The biometric results may drive communication relating to services available, and coordinate with data bases relating to preference information of the user. The communication protocols may enhance responses for safety, health, logistics and economic decisions of various kinds.

In a non-limiting example, the present invention utilizes biometric data gathered by any number of devices in conjunction with secondary and tertiary devices, including communication networks, to provide a user with a comprehensive means for health care maintenance. For example, an individual wearing a contact lens with a glucose sensor may have data generated by the sensor transmitted over a communication network to his or her cell phone as a possible alert to low or high sugar levels. Simultaneously therewith, a message may be automatically generated to alert a health care professional locate in the vicinity of the user of a possible medical emergency. The data collected may be forwarded to the health care professional so he or she will have it ready when the person arrives. A GPS application as part of the system would serve to provide the user's location.

More specifically, the present invention may retrieve targeted and individualized content based biometric data, environmental data, location data and a personalized preference determination calculated via predictive analytics to generate the targeted and individualized content.

In some examples, a biometric based information communication system comprises a wearable device that has the ability to detect a user's location, biometrics, and environment to provide targeted information communication.

In some examples, a biometric based information communication system comprises a wearable device that has the ability to detect a user's location, biometrics, environment, and weather to provide targeted information communication.

One general aspect includes a system for biometric based information communication including a biomedical device. The system also includes a sensing means. The system also includes an energization device. The system also includes a communication means; a communication hub, where the hub receives communication containing at least a data value from the biomedical device and transmits the communication to a content server; and a display.

Implementations may include one or more of the following features. The system may additionally include a user electronic device, where the user electronic device is paired in a communication protocol with the biomedical device. The system may include examples where the display is located on the user electronic device. The system may include examples where the display is located in the biomedical device. The system may include examples where the content server transmits a targeted message through a biometric information communication system to the display.

The system may include examples where the sensing means includes an element to monitor a user's temperature, and/or an element to monitor a user's pupil size, and/or an element to monitor a user's intraocular pressure, and/or an element to monitor a user's eye motion, and/or an element to monitor a user's blink rate, and/or an element to monitor a user's pulse, and/or an element to monitor a user's blood pressure. The system may include examples where the sensing means includes an element to monitor a user's blood oximetry level. The system may include examples where the sensing means includes an element to monitor a user's blood glucose level.

There may be methods where the system receives a second portion of the communication from the biometric measurement system communication system, where the second portion of the communication includes at least a data value corresponding to a user location.

Methods may additionally include tailoring the message data stream based upon the data value corresponding to the user location. In some methods, the first device includes a worn device. In some of these methods the first device includes a smart watch. There may be examples where the first device includes a worn biomedical device, and in some cases this worn biomedical device is a contact lens. Alternatively, the worn biomedical device may be a smart ring. The method may include examples where the second device includes a smart phone. Alternatively, the second device includes a smart watch. In further examples, the first device may include a sub-cutaneous biomedical device.

One general aspect includes a method to communicate a message, the method including: obtaining a biomedical device capable of performing a biometric measurement; utilizing the biomedical device to perform the biometric measurement; and receiving a message based upon a communication of a biometric data result obtained by the biometric measurement.

One general aspect includes a method to communicate a message, the method including: providing a biomedical device capable of performing a biometric measurement, receiving a communication from a biometric measurement system communication system, where the communication includes at least a data value corresponding to a biometric result obtained with the biomedical device, and processing the biometric result with a processor, where the processing generates a message data stream. The method may also include transmitting the message data stream to the biometric measurement system communication system.

Implementations may include one or more of the following features. The method may additionally include receiving a second portion of the communication from the biometric measurement system communication system, where the second portion of the communication includes at least a data value corresponding to a user location. The method additionally including tailoring the message data stream based upon the data value corresponding to the user location. The method may include examples where the first device includes a worn device. The method may include examples where the first device includes a smart watch. An example may be where the method where the first device includes a worn biomedical device. The method may include an example where the worn biomedical device is a contact lens. The method may additionally include examples where the worn biomedical device is a smart ring. The method may include examples where the second device includes a smart phone. The method may include examples where the second device includes a smart watch. The method may include examples where the first device includes a sub-cutaneous biomedical device.

One general aspect related to methods includes: obtaining a first device, where the first device is capable to measure at least a first biometric of a user; measuring the first biometric with the first device to obtain biometric data; determining a location of the first device with the first device to obtain location data; communicating the biometric data and the location data to a computing device connected to a network; authorizing the computing device, via a signal from the first device, to obtain environmental data related to the location data; authorizing the computing device to initiate an algorithm to be executed to retrieve a targeted and individualized content based on the biometric data, the environmental data, the location data and a personalized preference determination calculated via predictive analysis to generate the targeted and individualized content; receiving a message including the targeted and individualized content to the first device; and displaying the message to the user.

Implementations may include one or more of the following features. The method where the first device includes a worn device. The method may include examples where the first device includes a smart watch. The method may include examples where the first device includes a worn biomedical device. The method may include examples where the worn biomedical device is a contact lens. The method may include examples where the worn biomedical device is a smart ring. The method may include examples where the second device includes a smart phone. The method may include examples where the second device includes a smart watch. The method may include examples where the first device includes a sub-cutaneous biomedical device.

One general aspect related to methods includes: obtaining a first device, where the first device is capable to measure at least a first biometric of a user; measuring the first biometric with the first device to obtain biometric data; obtaining a second device, where the second device includes a display and a network communication device; authorizing a paired communication between the first device and the second device; communicating the biometric data from the first device to the second device; determining a location of the first device with the second device to obtain location data; communicating the biometric data and the location data to a computing device connected to a network; authorizing the computing device, via a signal from the first device, to obtain environmental data related to the location data; authorizing the computing device to initiate an algorithm to be executed to retrieve a targeted and individualized content based on the biometric data, the environmental data, the location data and a personalized preference determination calculated via predictive analysis to generate the targeted and individualized content; receiving a message including the targeted and individualized content to the second device; and displaying the message to the user.

BRIEF DESCRIPTION OF THE DRAWINGS

The foregoing and other features and advantages of the invention will be apparent from the following, more particular description of preferred embodiments of the invention, as illustrated in the accompanying drawings.

FIGS. 7A-7B illustrates an alternative biometric monitoring device.

DETAILED DESCRIPTION OF THE PREFERRED EMBODIMENTS

Glossary

Figure 1A:
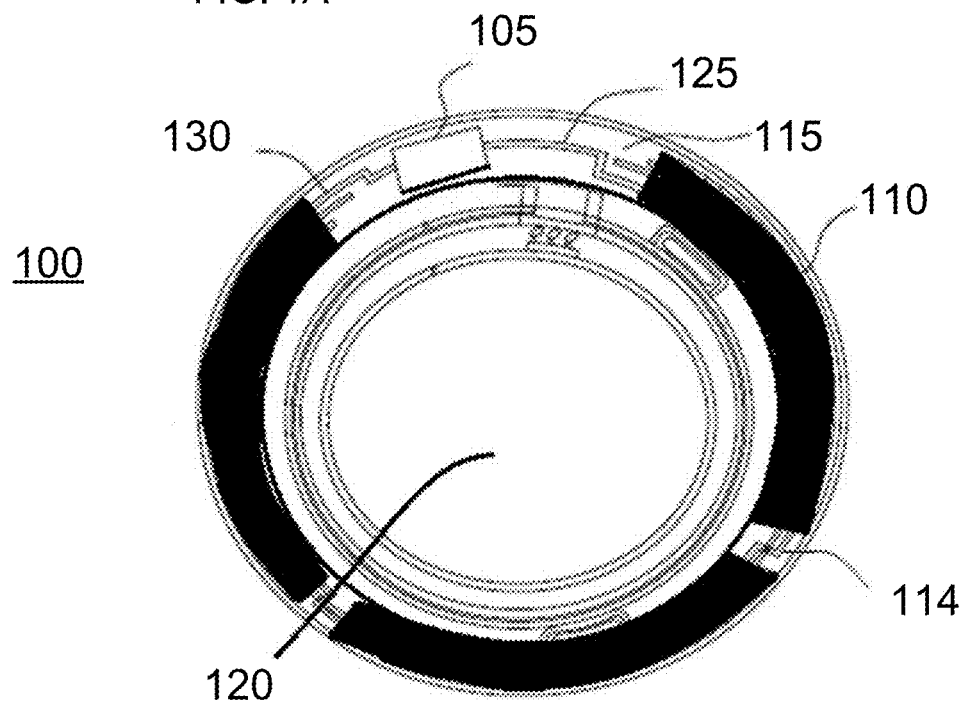
FIGS. 1A and 1B illustrate an exemplary biomedical device for exemplary description of the concepts of biometric based information communication.

Biometric or biometrics as used herein refers to the data and the collection of data from measurements performed upon biological entities. Typically, the collection of data may refer to human data relating to sizing, medical status, chemical and biochemical status and the like. In some examples, biometric data may derive from measurements performed by biosensors. In other examples, the measureable biological component or parameter may refer to a physiological characteristic such as temperature, blood pressure and the like.

Biosensor or biological sensor as used here refers to a system including a biological component or bioelement such as an enzyme, antibody, protein, or nucleic acid. The bioelement interacts with the analyte and the response is processed by an electronic component that measures or detects the measureable biological response and transmits the obtained result. When the bioelement binds to the analyte, the sensor may be called an affinity sensor. When the analyte is chemically transformed by the bioelement the sensor may be called a metabolic sensor. Catalytic biosensors may refer to a biosensor system based on the recognition of a molecular analyte by the bioelement which leads to conversion of an auxiliary substrate into something that may be detected.

Biometric Based Information Communication

Biomedical devices for biometric based information communication are disclosed in this application. In the following sections, detailed descriptions of various embodiments are described. The description of both preferred and alternative embodiments are exemplary embodiments only, and various modifications and alterations may be apparent to those skilled in the art. Therefore, the exemplary embodiments do not limit the scope of this application. The biomedical devices for biometric based information communication are designed for use in, on, or proximate to the body of a living organism. One example of such a biomedical device is an ophthalmic device such as a contact lens.

Recent developments in biomedical devices, including for example ophthalmic devices, have occurred enabling functionalized biomedical devices that may be energized. These energized biomedical devices have the ability to enhance a user's health by providing up-to-date feedback on the homeostatic patterns of the body and enhancing a user's experience in interacting with the outside world and the internet. These enhancements may be possible through the use of biomedical devices for biometrics based information communication.

Biomedical devices for biometrics based information communication may be useful for projecting personalized content to a user device based on a collection of data from that user including information such as online surfing and shopping tendencies, in-person shopping and browsing tendencies, dietary habits, biomarkers such as metabolites, electrolytes, and pathogens, and biometrics information such as heart rate, blood pressure, sleep cycles, and blood-sugar as non-limiting examples. The data collected may be analyzed and used by the user, or third-parties such as medical care personnel, in order to predict future behavior, suggest changes to current habits, and propose new items or habits for the user.

Biomedical Devices to Collect Biometric Data

There may be numerous types of biomedical devices that may collect diverse types of biometric data. Some devices may correspond to remote sensors that measure and observe a human subject from afar, such as cameras, electromagnetic spectral sensors, scales and microphones as non-limiting examples. Other devices may be worn by a user in various manners. In some examples, smart devices may be worn and have ability to collect biometric data such as on bands on wrists, arms and legs; rings on fingers, toes and ears; contact lenses on eyes; hearing aids in ear canals; and clothing on various parts of the body. Other examples may include, implanted biomedical devices of various types such as pacemakers, stents, ocular implants, aural implants, and generalized subcutaneous implants.

Energized Ophthalmic Device

One type of device that may be utilized in connection with the present invention is an energized ophthalmic device. Referring to FIG. 1A, an exemplary embodiment of a media insert 100 for an energized ophthalmic device and a corresponding energized ophthalmic device 150 (FIG. 1B) are illustrated. The media insert 100 may comprise an optical zone 120 that may or may not be functional to provide vision correction. Where the energized function of the ophthalmic device is unrelated to vision, the optical zone 120 of the media insert may be void of material. In some exemplary embodiments, the media insert may include a portion not in the optical zone 120 comprising a substrate 115 incorporated with energization elements 110 (power source) and electronic components 105 (load).

In some exemplary embodiments, a power source, for example, a battery, and a load, for example, a semiconductor die, may be attached to the substrate 115. Conductive traces 125 and 130 may electrically interconnect the electronic components 105 and the energization elements 110 and energization elements may be electrically interconnected such as by conductive traces 114. The media insert 100 may be fully encapsulated to protect and contain the energization elements 110, traces 125, and electronic components 105. In some exemplary embodiments, the encapsulating material may be semi-permeable, for example, to prevent specific substances, such as water, from entering the media insert and to allow specific substances, such as ambient gasses or the byproducts of reactions within energization elements, to penetrate or escape from the media insert.

Figure 1B:
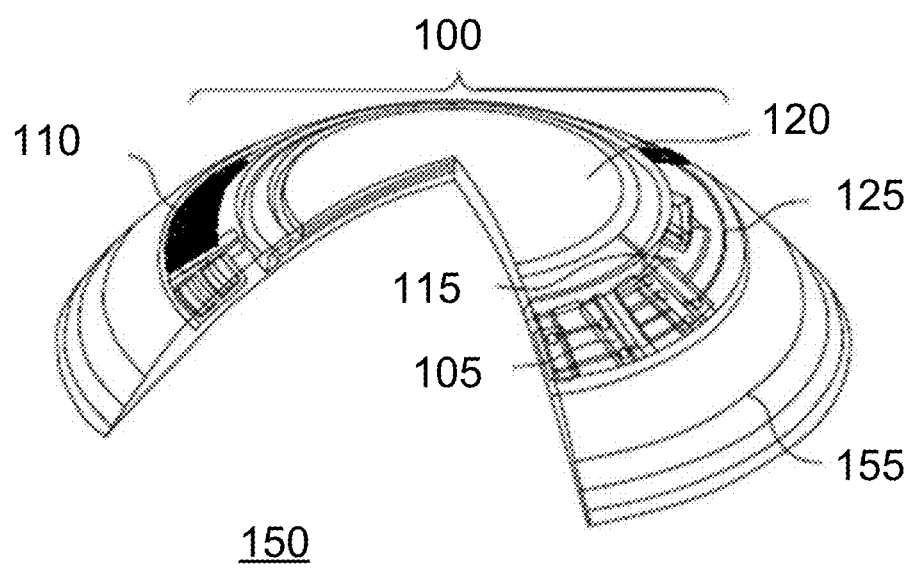

In some exemplary embodiments, as depicted in FIG. 1B, the media insert 100 may be included in an ophthalmic device 150, which may comprise a polymeric biocompatible material. The ophthalmic device 150 may include a rigid center, soft skirt design wherein the central rigid optical element comprises the media insert 100. In some specific embodiments, the media insert 100 may be in direct contact with the atmosphere and the corneal surface on respective anterior and posterior surfaces, or alternatively, the media insert 100 may be encapsulated in the ophthalmic device 150. The periphery 155 of the ophthalmic device 150 or lens may be a soft skirt material, including, for example, a hydrogel material. The infrastructure of the media insert 100 and the ophthalmic device 150 may provide an environment for numerous embodiments involving fluid sample processing by numerous analytical techniques such as with fluorescence based analysis elements in a non-limiting example.

Personalized Information Communication

Various aspects of the technology described herein are generally directed to systems, methods, and computer-readable storage media for providing personalized content. Personalized content, as used herein, may refer to advertisements, organic information, promotional content, or any other type of information that is desired to be individually directed to a user. The personalized content may be provided by, for example, a target content provider, such as an advertising provider, an informational provider, and the like. Utilizing embodiments of the present invention, the user or a content provider may select specific content that it would like to target. The relevant information may be detected by the device, and because of the self-contained power of the device, computed or analyzed to produce relevant personal information. Once analyzed, the personalized content may then be presented to the user by the device.

Predictive Analytics

Computing systems may be configured to track the behaviors of an individual. The computing system may then compile one or more user specific reports based on the information collected. These reports may then be sent to the user, or sent to another device to use the gathered information in conjunction with other behavior based reports to compile new, more in depth behavioral based reports. These in-depth behavior based reports may capture certain preferred behaviors, trends, habits, and the like for the individual which may be used to infer future preferred behaviors or tendencies. This practice may be referred to as predictive analytics.

Predictive analytics encompasses a variety of statistical techniques from modeling, machine learning, and data mining that analyze current and historical facts to make predictions about future, or otherwise unknown, events. One example of predictive analytics may be that an individual has recently searched the internet for popular Caribbean destinations. The individual has also searched the internet for cheap airfare. This information may be compiled and used to find the cheapest all-inclusive packages to Caribbean destinations purchased by all internet users within the last month.

Storage of Behavioral Information

There may be a need to store behavioral information for future use. The information may be stored locally, on the device collecting the information, or remotely stored as computer readable media. Such computer readable media may be associated with user profile information so that the user can access and/or utilize the behavioral information on other computing devices. In some instances, the devices and the storage media may need to communicate with one or more other devices or storage media.

Figure 2:
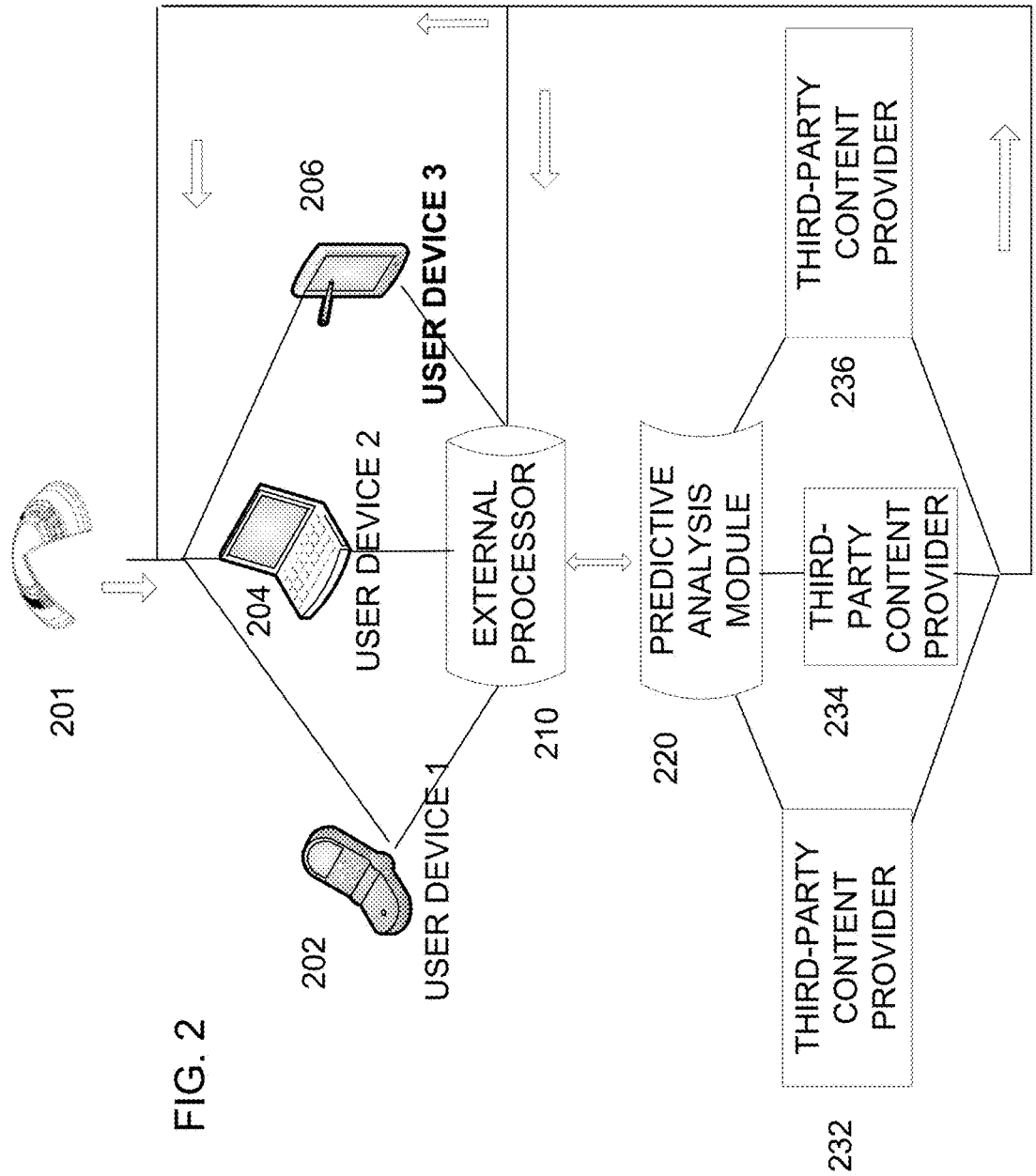
FIG. 2 illustrates an exemplary network of biomedical, user and data processing devices consistent with the concepts of biometric based information communication.

A communication network may allow tasks to be performed remotely. In a distributed computing environment, program modules may be located in both local and remote computer storage media including memory storage devices. The computer-usable instructions form an interface to allow a computer to react according to a source of input. The instructions operate with other code segments to initiate a variety of tasks in response to data received in conjunction with the source of the received data. FIG. 2 illustrates an example of a communication network between devices and storage elements. A biomedical device 201, for example an ophthalmic device, may provide biometric and other type of data to the communication network. In some examples, a first user device 202, such as a smart phone, may be used to gather user information such as favorite websites and shopping tendencies. The first user device 202 may also receive data from the biomedical device 201 and this data may be correlated with other user information. The same may be accomplished by a secondary user device 204, such as a personal computer, or a tertiary device 206, such as a tablet. Once this information is collected, it may either be stored in the device itself, or transferred out to an external processor 210. The external processor 210 may be, for example, a cloud based information storage system. The stored information may then be sent to and processed by a predictive analysis module 220 for analysis on how past user tendencies and events may predict future user tendencies and events. Such a module 220 may be provided by, for example, an existing third-party specializing in predictive analytics. The processed information may then be sent back to the external processor 210 as readily available predictor information for a user device. Alternatively, the processed information may be received by one or several third-party content providers 232, 234, 236. Once received by a third-party content provider, the third party may tailor their advertising to the personality of the user. For example, a car dealership selling several different types of vehicles may advertise only their selection of sports cars to a user that has recently been surfing the internet for sports cars. This personalized content may then be sent directly to the user, or may be stored in an external processor 210 for later retrieval by the user.

Storage-media-to-device communication may be accomplished via computer readable media. Computer readable media may be any available media that may be assessed by a computing device and may include both volatile and nonvolatile media, removable and non-removable media. Computer readable media may comprise computer storage media and communication media. Computer storage media may include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computing device.

Communication media may include computer-readable instructions, data structures, program modules or other or other data in a modulated data signal such as a carrier wave or other transport mechanism and may include any information delivery media. A modulated data signal may include a signal that has one or more of its characteristics set or changed in such a manner as to encode information in the signal. For example, communication media may include wired media such as wired network or direct-wired connection, and wireless media such as acoustic, RF, infrared, and other wireless media. Combinations of any of the above should also be included within the scope of computer-readable media.

Third Party Use of Behavioral Information

One advantage of compiling and storing behavioral information may be its use by third parties for individualized content. Third parties may gain consent to access to the stored behavioral information for use in a variety of ways including: emergency medical response, personalized medicine, information communication, activity tracking, navigation, and the like. One or more third parties may register with the device or the network of devices via a user interface. Once registered, the third parties may communicate with the user via the network and may gain access to all or some, in the user's discretion, of the behavioral data stored in the behavioral information storage system.

One exemplary embodiment of the disclosed personalized content display system may enable a device to track a user's preferred websites, spending habits, daily agenda, personal goals, and the like and store this information in a cloud. The cloud may be accessible by third party advertisers, and may be used by such third parties for predictive analysis. The third parties may predict future interesting websites, habits, proposed agendas, personal goals, and the like and send these proposals to the device to be viewed by the user.

More than one personalized content provider may target the same user. In one example, the user may have preferential settings that allow only certain types of content, thereby yielding an optimized user experience. The personalized content may be delivered to the user in several ways, utilizing one or more senses including sight, sound, touch, taste, and smell. Further, the personalized content may be delivered to an array of devices configured for use by the user including biomedical devices, cell-phones, computers, tablets, wearable technology, and the like.

Environmental Data Sources

Environmental data organized by geographic regions are readily available in network access manners. Weather systems organized by various providers of such data may link various environmental data such as temperature, humidity, pressure, precipitation, solar incidence, and other such data. Networked weather stations of individuals and companies provide refined geographic data on a local basis. And, advanced satellite systems provide environmental data from global scale to regional scales. Finally, sophisticated modelling systems use the regionally recorded data and project environmental data into the future. Environmental data may in some examples be tied to the other types of data herein to establish a targeted communication.

Diagrams for Electrical and Computing System

Figure 3:
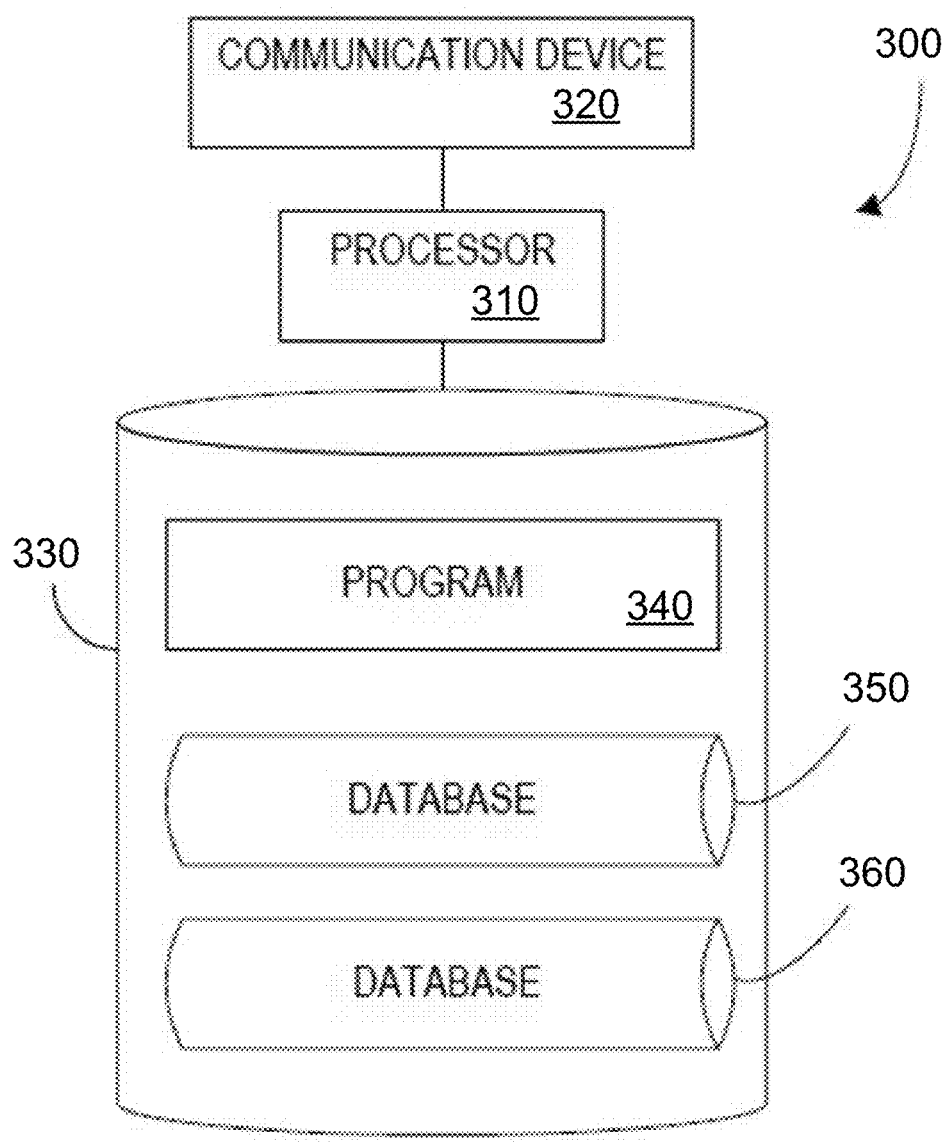
FIG. 3 illustrates a processor that may be used to implement some embodiments of the present invention.

Referring now to FIG. 3, a schematic diagram of a processor that may be used to implement some aspects of the present disclosure is illustrated. A controller 300 may include one or more processors 310, which may include one or more processor components coupled to a communication device 320. In some embodiments, a controller 300 may be used to transmit energy to the energy source placed in the device.

The processors 310 may be coupled to a communication device 320 configured to communicate energy via a communication channel. The communication device 320 may be used to electronically communicate with components within the media insert, for example. The communication device 320 may also be used to communicate, for example, with one or more controller apparatus or programming/interface device components.

The processor 310 is also in communication with a storage device 330. The storage device 330 may comprise any appropriate information storage device, including combinations of magnetic storage devices, optical storage devices, and/or semiconductor memory devices such as Random Access Memory (RAM) devices and Read Only Memory (ROM) devices.

The storage device 330 may store a program or programs 340 for controlling the processor 310. The processor 310 performs instructions of a software program 340, and thereby operates in accordance with the present invention. For example, the processor 310 may receive information descriptive of media insert placement, and active target zones of the device. The storage device 330 may also store other pre-determined biometric related data in one or more databases 350 and 360. The biometric data may include, for example, predetermined retinal zones exhibiting changes according to cardiac rhythm or an abnormal condition correlated with the retinal vascularization, measurement thresholds, metrology data, and specific control sequences for the system, flow of energy to and from a media insert, communication protocols, and the like. The database may also include parameters and controlling algorithms for the control of the biometric based monitoring system that may reside in the device as well as data and/or feedback that can result from their action. In some embodiments, that data may be ultimately communicated to/from an external reception wireless device.

Systems and Device Structure for Biometric Sensors and Communications

Exemplary devices to perform the present invention may have significant complexity. In some embodiments, solutions to carry out the various functions may be implemented in small biomedical device form factors through the co-integration of devices into components and through the stacking of the various components.

In some embodiments according to aspects of the present invention, a single and/or multiple discrete electronic devices may be included as discrete chips. In other embodiments, energized electronic elements may be included in a media insert (see FIGS. 1A and 1B) in the form of stacked integrated components. Accordingly, and referring now to FIG. 4, a schematic diagram of an exemplary cross section of stacked die integrated components implementing a biometric based monitoring system 410 is depicted with a biometric sensing layer 411. The biometric based tracking system may be, for example, a glucose monitor, a retinal vascularization monitor, a visual scanning monitor, a GPS or location based tracking monitor, or any other type of system useful for providing information about the user. In particular, a media insert may include numerous layers of different types which are encapsulated into contours consistent with the environment that they will occupy. In some embodiments, these media inserts with stacked integrated component layers may assume the entire shape of the media insert. Alternatively in some cases, the media insert may occupy just a portion of the volume within the entire shape.

Figure 4:
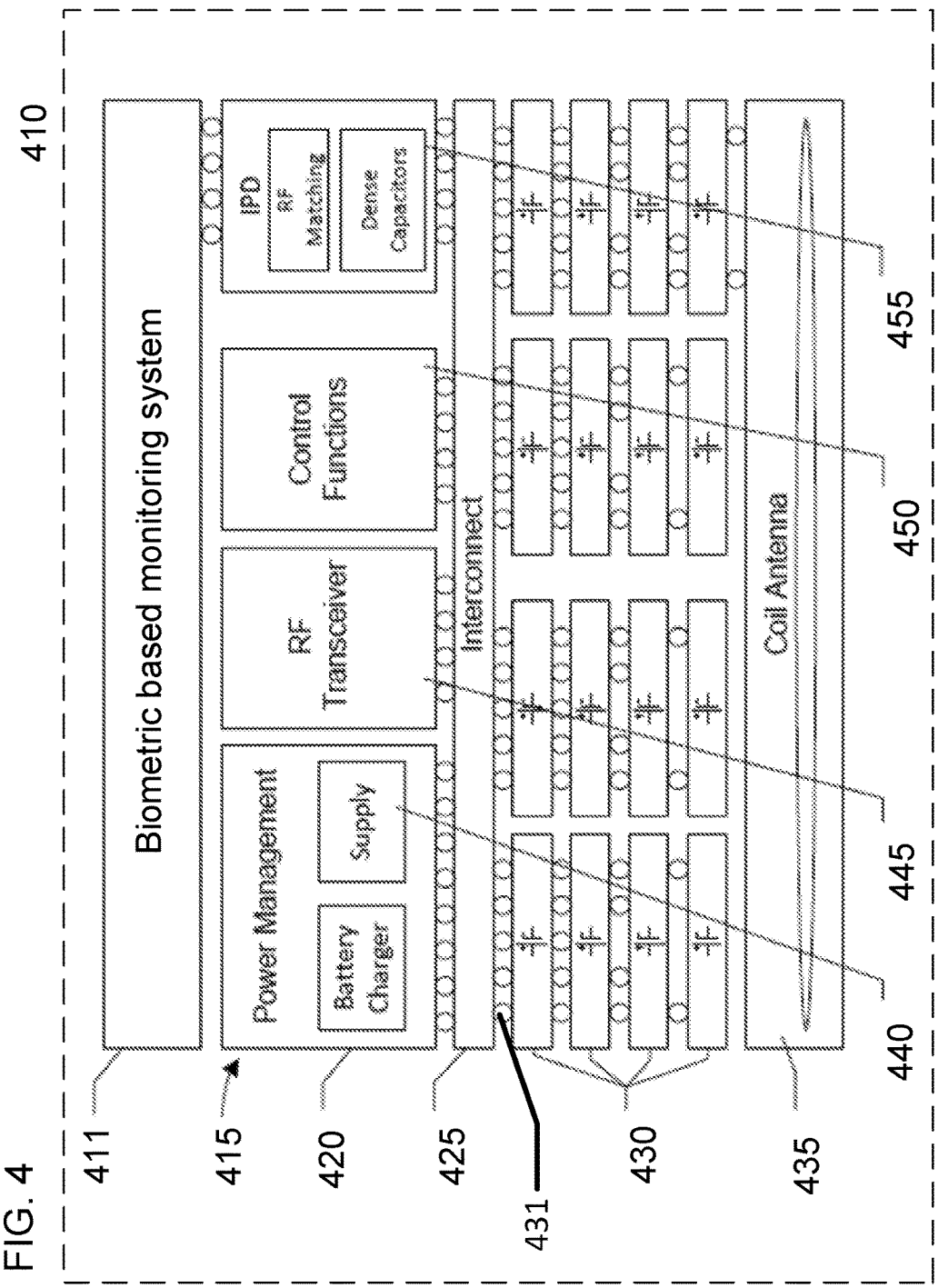
FIG. 4 illustrates an exemplary functional structure model for a biomedical device for a biometric based monitoring.

As shown in FIG. 4, there may be thin film batteries 430 used to provide energization. In some embodiments, these thin film batteries 430 may comprise one or more of the layers that can be stacked upon each other with multiple components in the layers and interconnections there between. The batteries are depicted as thin film batteries 430 for exemplary purposes, there may be numerous other energization elements consistent with the embodiments herein including operation in both stacked and non-stacked embodiments. As a non-limiting alternative example, cavity based laminate form batteries with multiple cavities may perform equivalently or similarly to the depicted thin film batteries 430.

In some embodiments, there may be additional interconnections between two layers that are stacked upon each other. In the state of the art there may be numerous manners to make these interconnections; however, as demonstrated the interconnection may be made through solder ball interconnections between the layers. In some embodiments only these connections may be required; however, in other cases the solder balls 431 may contact other interconnection elements, as for example with a component having through layer vias.

In other layers of the stacked integrated component media insert, a layer 425 may be dedicated for the interconnections two or more of the various components in the interconnect layers. The interconnect layer 425 may contain, vias and routing lines that can pass signals from various components to others. For example, interconnect layer 425 may provide the various battery elements connections to a power management unit 420 that may be present in a technology layer 415. The power management unit 420 may include circuitry to receive raw battery supply conditions and output to the rest of the device standard power supply conditions from the output of supply 440. Other components in the technology layer 415 may include, for example, a transceiver 445, control components 450 and the like. In addition, the interconnect layer 425 may function to make connections between components in the technology layer 415 as well as components outside the technology layer 415; as may exist for example in the integrated passive device 455. There may be numerous manners for routing of electrical signals that may be supported by the presence of dedicated interconnect layers such as interconnect layer 425.

In some embodiments, the technology layer 415, like other layer components, may be included as multiple layers as these features represent a diversity of technology options that may be included in media inserts. In some embodiments, one of the layers may include CMOS, BiCMOS, Bipolar, or memory based technologies whereas the other layer may include a different technology. Alternatively, the two layers may represent different technology families within a same overall family, as for example one layer may include electronic elements produced using a 0.5 micron CMOS technology and another layer may include elements produced using a 20 nanometer CMOS technology. It may be apparent that many other combinations of various electronic technology types would be consistent within the art described herein.

In some embodiments, the media insert may include locations for electrical interconnections to components outside the insert. In other examples; however, the media insert may also include an interconnection to external components in a wireless manner. In such cases, the use of antennas in an antenna layer 435 may provide exemplary manners of wireless communication. In many cases, such an antenna layer 435 may be located, for example, on the top or bottom of the stacked integrated component device within the media insert.

In some of the embodiments discussed herein, the energization elements which have heretofore been called thin film batteries 430 may be included as elements in at least one of the stacked layers themselves. It may be noted as well that other embodiments may be possible where the battery elements are located externally to the stacked integrated component layers. Still further diversity in embodiments may derive from the fact that a separate battery or other energization component may also exist within the media insert, or alternatively these separate energization components may also be located externally to the media insert. In these examples, the functionality may be depicted for inclusion of stacked integrated components, it may be clear that the functional elements may also be incorporated into biomedical devices in such a manner that does not involve stacked components and still be able to perform functions related to the embodiments herein.

Components of the biometric based monitoring system 410 may also be included in a stacked integrated component architecture. In some embodiments, the biometric based monitoring system 410 components may be attached as a portion of a layer. In other embodiments, the entire biometric based monitoring system 410 may also comprise a similarly shaped component as the other stacked integrated components. In some alternative examples, the components may not be stacked but layed out in the peripheral regions of the ophthalmic device or other biomedical device, where the general functional interplay of the components may function equivalently however the routing of signals and power through the entire circuit may differ.

Biomarkers/Analytical Chemistry

A biomarker, or biological marker, generally refers to a measurable indicator of some biological state or condition. The term is also occasionally used to refer to a substance the presence of which indicates the existence of a living organism. Further, life forms are known to shed unique chemicals, including DNA, into the environment as evidence of their presence in a particular location. Biomarkers are often measured and evaluated to examine normal biological processes, pathogenic processes, or pharmacologic responses to a therapeutic intervention. In their totality, these biomarkers may reveal vast amounts of information important to the prevention and treatment of disease and the maintenance of health and wellness.

Biomedical devices configured to analyze biomarkers may be utilized to quickly and accurately reveal one's normal body functioning and assess whether that person is maintaining a healthy lifestyle or whether a change may be required to avoid illness or disease. Biomedical devices may be configured to read and analyze proteins, bacteria, viruses, changes in temperature, changes in pH, metabolites, electrolytes, and other such analytes used in diagnostic medicine and analytical chemistry.

Fluorescence Based Probe Elements for Analyte Analysis

Various types of analytes may be detected and analyzed using fluorescence based analysis techniques. A subset of these techniques may involve the direct fluorescence emission from the analyte itself. A more generic set of techniques relate to fluorescence probes that have constituents that bind to analyte molecules and in so alter a fluorescence signature. For example, in Förster Resonance Energy Transfer (FRET), probes are configured with a combination of two fluorophores that may be chemically attached to interacting proteins. The distance of the fluorophores from each other can affect the efficiency of a fluorescence signal emanating therefrom.

One of the fluorophores may absorb an excitation irradiation signal and can resonantly transfer the excitation to electronic states in the other fluorophore. The binding of analytes to the attached interacting proteins may disturb the geometry and cause a change in the fluorescent emission from the pair of fluorophores. Binding sites may be genetically programmed into the interacting proteins, and for example, a binding site, which is sensitive to glucose, may be programmed. In some cases, the resulting site may be less sensitive or non-sensitive to other constituents in interstitial fluids of a desired sample.

The binding of an analyte to the FRET probes may yield a fluorescence signal that is sensitive to glucose concentrations. In some exemplary embodiments, the FRET based probes may be sensitive to as little as a 10 uM concentration of glucose and may be sensitive to up to hundreds of micromolar concentrations. Various FRET probes may be genetically designed and formed. The resulting probes may be configured into structures that may assist analysis of interstitial fluids of a subject. In some exemplary embodiments, the probes may be placed within a matrix of material that is permeable to the interstitial fluids and their components, for example, the FRET probes may be assembled into hydrogel structures. In some exemplary embodiments, these hydrogel probes may be included into the hydrogel based processing of ophthalmic contact lenses in such a manner that they may reside in a hydrogel encapsulation that is immersed in tear fluid when worn upon the eye. In other exemplary embodiments, the probe may be inserted in the ocular tissues just above the sclera. A hydrogel matrix comprising fluorescence emitting analyte sensitive probes may be placed in various locations that are in contact with bodily fluids containing an analyte.

In the examples provided, the fluorescence probes may be in contact with interstitial fluid of the ocular region near the sclera. In these cases, where the probes are invasively embedded, a sensing device may provide a radiation signal incident upon the fluorescence probe from a location external to the eye such as from an ophthalmic lens or a hand held device held in proximity to the eye.

In other exemplary embodiments, the probe may be embedded within an ophthalmic lens in proximity to a fluorescence-sensing device that is also embedded within the ophthalmic lens. In some exemplary embodiments, a hydrogel skirt may encapsulate both an ophthalmic insert with a fluorescence detector as well as a FRET based analyte probe.

Ophthalmic Insert Devices and Ophthalmic Devices with Fluorescence Detectors

Figure 5:
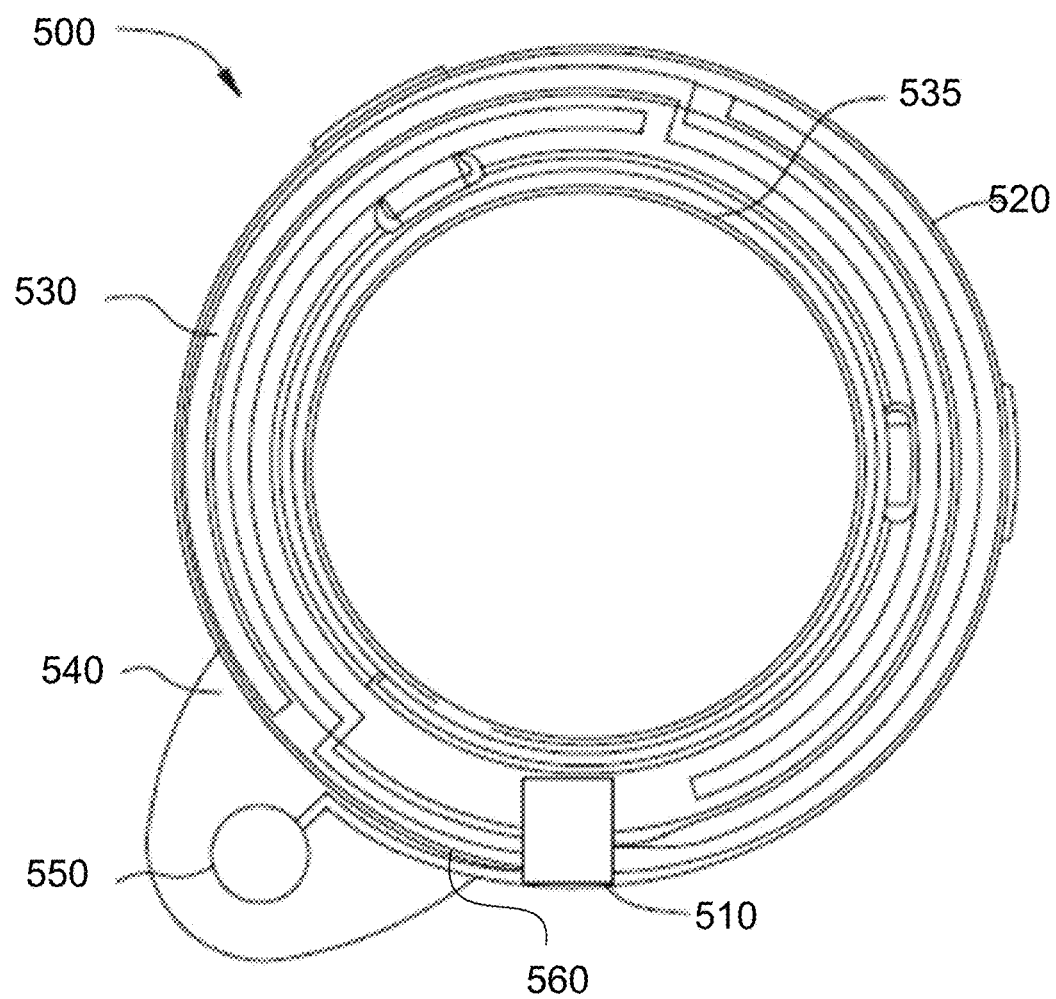
FIG. 5 illustrates an exemplary fluorescence based biometric monitoring device.

Referring to FIG. 5, an ophthalmic insert 500 is demonstrated including components that may form an exemplary fluorescence based analytical system. The demonstrated ophthalmic insert 500 is shown in an exemplary annular form having an internal border of 535 and an external border of 520. In addition to energization elements 530, powered electronic components 510, and interconnect features 560 there may be a fluorescence analytical system 550, which in certain exemplary embodiments may be positioned on a flap 540. The flap 540 may be connected to the insert 500 or be an integral, monolithic extension thereof. The flap 540 may properly position the fluorescence analytical system 550 when an ophthalmic device comprising a fluorescence detector is worn. The flap 540 may allow the analytical system 550 to overlap with portions of the user's eye away from the optic zone. The fluorescence based analytical system 550 may be capable of determining an analyte, in terms of its presence or its concentration, in a fluid sample. As a non-limiting example, the fluorophores may include Fluorescein, Tetramethylrhodamine, or other derivatives of Rhodamine and Fluorescein. It may be obvious to those skilled in the art that any fluorescence emitting analyte probe, which may include fluorophore combinations for FRET or other fluorescence-based analysis may be consistent with the art herein.

For a fluorescence analysis, a probe may be irradiated with an excitation light source. This light source may be located within the body of the analytical system 550. In some exemplary embodiments, the light source may comprise a solid-state device or devices such as a light emitting diode. In an alternative exemplary embodiment, an InGaN based blue laser diode may irradiate at a frequency corresponding to a wavelength of 442 nm for example. Nanoscopic light sources as individual or array sources may be formed from metallic cavities with shaped emission features such as bowties or crosses. In other exemplary embodiments, light emitting diodes may emit a range of frequencies at corresponding wavelengths that approximate 440 nm, for example. As well, the emission sources may be supplemented with a band pass filtering device in some embodiments.

Other optical elements may be used to diffuse the light source from the solid-state device as it leaves the insert device. These elements may be molded into the ophthalmic insert body itself. In other exemplary embodiments, elements such as fiber optic filaments may be attached to the insert device to function as a diffuse emitter.

There may be numerous means to provide irradiation to a fluorescence probe from an ophthalmic insert device 500 of the type demonstrated in FIG. 5.

A fluorescence signal may also be detected within the fluorescence based analytical system 550. A solid-state detector element may be configured to detect light in a band around 525 nm as an example. The solid-state element may be coated in such a manner to pass only a band of frequencies that is not present in the light sources that have been described. In other exemplary embodiments, the light sources may have a duty cycle and a detector element's signal may only be recorded during periods when the light source is in an off state. When the duty cycle is used, detectors with wide band detection ability may be advantageous.

An electronic control bus of interconnects 560 shown schematically may provide the signals to the light source or sources and return signals from the detectors. The powered electronic component 510 may provide the signals and power aspects. The exemplary embodiment of FIG. 5, illustrates a battery power source for energization elements 530 to the electronic circuitry which may also be called control circuitry. In other exemplary embodiments, energization may also be provided to the electronic circuitry by the coupling of energy through wireless manners such as radiofrequency transfer or photoelectric transfer.

Further enablement for the use of fluorescence detectors in biomedical devices may be found as set forth in U.S. patent application Ser. No. 14/011,902 filed Aug. 28, 2013, which is incorporated herein by reference.

Ophthalmic Lens with Event Coloration Mechanism

Another method of detecting analytes may be a passive coloration scheme wherein analytes may strictly bind to a reactive compound resulting in a color change which may indicate the presence of a specific analyte.

In some embodiments, an event coloration mechanism may comprise a reactive mixture, which, for example, may be added to, printed on, or embedded in a rigid insert of an ophthalmic device, such as through thermoforming techniques. Alternatively, the event coloration mechanism may not require a rigid insert but instead may be located on or within a hydrogel portion, for example, through use of printing or injection techniques.

The event coloration mechanism may comprise a portion of a rigid insert that is reactive to some component of the transient tear fluid or some component within an ophthalmic lens. For example, the event may be a specific accumulation of some precipitant, such as, lipids or proteins, on either or both the rigid ophthalmic insert and a hydrogel portion, depending on the composition of the ophthalmic lens. The accumulation level may "activate" the event coloration mechanism without requiring a power source. The activation may be gradual wherein the color becomes more visible as the accumulation level increases, which may indicate when the ophthalmic lens needs to be cleaned or replaced.

Alternatively, the color may only be apparent at a specific level. In some embodiments, the activation may be reversible, for example, where the wearer effectively removes the precipitant from the hydrogel portion or the rigid insert. The event coloration mechanism may be located outside the optic zone, which may allow for an annular embodiment of the rigid insert. In other embodiments, particularly where the event may prompt a wearer to take immediate action, the event coloration mechanism may be located within the optic zone, allowing the wearer to see the activation of the event coloration mechanism.

In some other embodiments, the event coloration mechanism, may comprise a reservoir containing a colored substance, for example, a dye. Prior to the occurrence of the event, the reservoir may not be visible. The reservoir may be encapsulated with a degradable material, which may be irreversibly degraded by some constituent of the tear fluid, including, for example, proteins or lipids. Once degraded, the colored substance may be released into the ophthalmic lens or into a second reservoir. Such an embodiment may indicate when a disposable ophthalmic lens should be disposed of, for example, based on a manufacturer's recommended parameters.

Figure 6A:
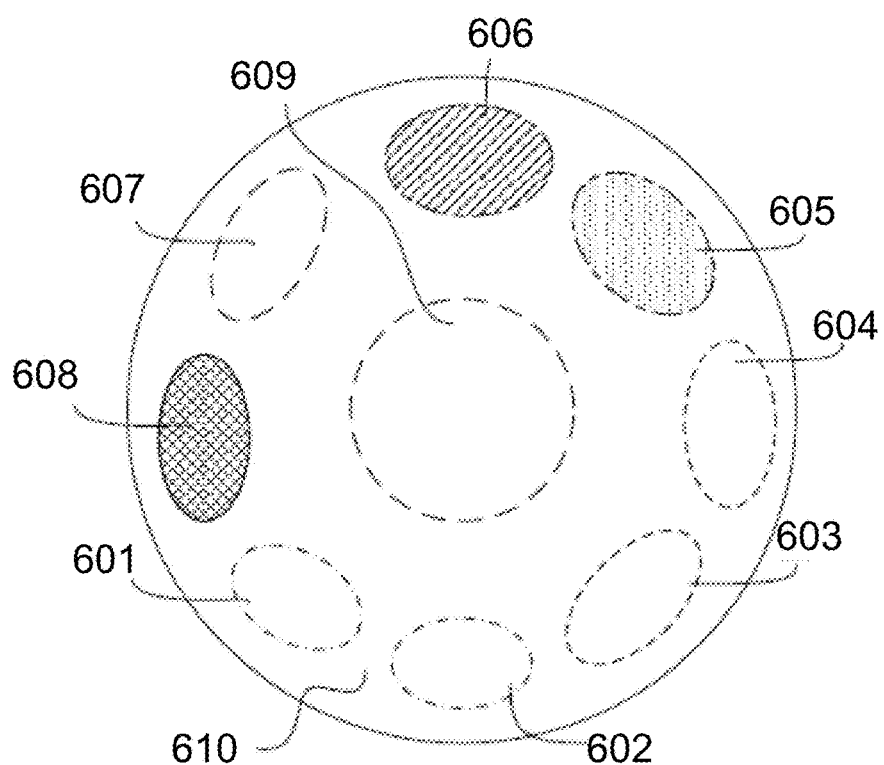
FIG. 6A-6B illustrates an exemplary colorimetric based biometric monitoring device.
Figure 6B:
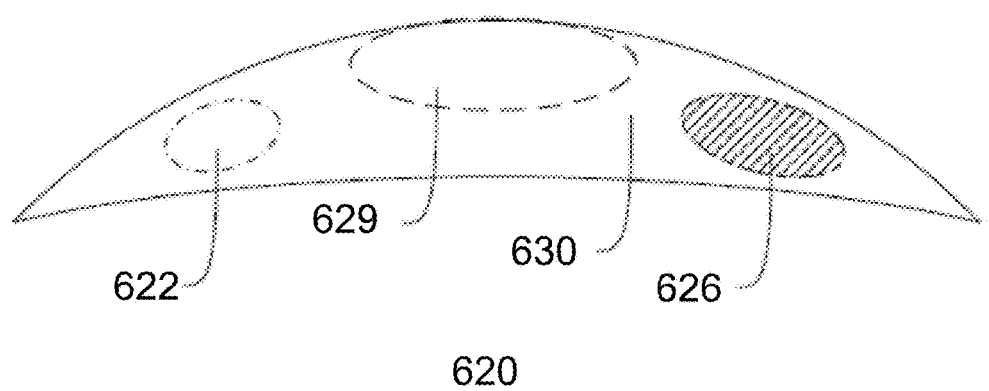

Proceeding to FIGS. 6A and 6B, an exemplary embodiment of an ophthalmic lens 600 with multiple event coloration mechanisms 601-608 is illustrated. In some embodiments, the event coloration mechanisms 601-608 may be located within the soft, hydrogel portion 610 of the ophthalmic lens 600 and outside the optic zone 609.

Such embodiments may not require a rigid insert or media insert for functioning of the event coloration mechanisms 601-608, though inserts may still be incorporated in the ophthalmic lens 600 allowing for additional functionalities. In some embodiments, each event coloration mechanism 601-608 may be separately encapsulated within the soft, hydrogel portion 610 of the ophthalmic lens 600. The contents of the event coloration mechanisms 601-608 may include a compound reactive to some condition, such as temperature, or component of tear fluid, such as a biomarker.

In some embodiments, each event coloration mechanism 601-608 may "activate" based on different events. For example, one event coloration mechanism 608 may comprise liquid crystal that may react to changes in temperatures of the ocular environment, wherein the event is a fever. Other event coloration mechanisms 602-606 within the same ophthalmic lens 600 may react to specific pathogens, for example, those that may cause ocular infections or may be indicative of non-ocular infections or diseases, such as keratitis, conjunctivitis, corneal ulcers, and cellulitis. Such pathogens may include, for example, *Acanthamoeba keratitis*, *Pseudomona aeruginosa*, *Neisseria gonorrhoeae*, and *Staphylococcus* and *Streptococcus* strains, such as *S. aureus*. The event coloration mechanisms 601-607 may be encapsulated with a compound that may be selectively permeable to a component of tear fluid. In some embodiments, the event coloration mechanisms 602-606 may function by agglutination, such as through a coagulase test, wherein a higher concentration of the pathogen may adhere to a compound within the event coloration mechanisms 602-606 and may cause clumping or the formation of precipitate. The precipitate may provide coloration or may react with another compound in the event coloration mechanisms 602-606 through a separate reaction. Alternatively, the event coloration mechanisms 602-606 may comprise a reagent that colors upon reaction, such as with some oxidase tests.

In still other embodiments, an event coloration mechanism 602-606 may function similarly to a litmus test, wherein the event coloration mechanism activates based on the pH or pOH within the ocular environment. For example, to monitor the concentration of valproic acid, the event coloration mechanism may contain specific proteins that would be able to bind to the valproic acid up to a specific concentration. The non-binding valproic acid may be indicative of the effective quantities within the tear fluid. The pH or pOH within the event coloration mechanism may increase with the increased concentration of the acid.

Other exemplary coloration mechanisms 601 may be reactive to ultraviolet rays, wherein the event may be overexposure of the eye to UV light, as with snow blindness. Another coloration mechanism 607 may react to protein accumulation, such as described with FIG. 6. Some event coloration mechanisms 608 may be reversible, such as when the wearer has effectively responded to the event. For example, after a wearer has rinsed the ophthalmic lens 600, the level of pathogens or protein may be sufficiently reduced to allow for safe use of the ophthalmic lens 600. Alternatively, the coloration may be reversible on the eye, such as where the event is a fever and the wearer's temperature has been effectively lowered.

As shown in cross section in FIG. 6B, the event coloration mechanisms 622, 626 may be located in the periphery of the ophthalmic lens 620 without altering the optical surface of the hydrogel portion 630. In some embodiments, not shown, the event coloration mechanisms may be at least partially within the optic zone 629, alerting the wearer of the event. The locations of the event coloration mechanisms 622, 626 may be varied within a single ophthalmic lens 620, with some in the periphery and some within the optic zone 629.

Referring again to FIG. 6A, the event coloration mechanisms 601-608 may be independently activated. For example, the wearer may have a fever, triggering a change in coloration in liquid crystal contained in an event coloration mechanism 608. Two other event coloration mechanisms 605, 606 may indicate high levels of *S. aureus* and *A. keratitis*, which may provide guidance on what is causing the fever, particularly where other symptoms corroborate the diagnosis. Where the event coloration mechanisms 601-608 serve as diagnostic tools, the coloration may not be reversible, allowing the wearer to remove the ophthalmic lens 600 without losing the event indication.

In some embodiments, the event coloration mechanism 608 may be coated in a substance with low permeability, such as, for example, parylene. This embodiment may be particularly significant where the event coloration mechanism 608 contains compounds that may be dangerous if in contact with the eye or where the event does not require interaction with the tear fluid. For example, where the event is a temperature change, a liquid crystal droplet may be parylene coated, which may be further strengthened into a hermetic seal by alternating the parylene with a fortifying compound, such as, silicon dioxide, gold, or aluminum.

For exemplary purposes, the ophthalmic lens 600 is shown to include eight event coloration mechanisms. However, it may be obvious to those skilled in the art that other quantities of event coloration mechanisms may be practical. In some examples, a photoactive detector may be located inside the region of the event coloration mechanism within the ophthalmic lens insert device. The photoactive detector may be formed to be sensitive to the presence of light in the spectrum of the coloration mechanism. The photoactive detector may monitor the ambient light of a user and determine a baseline level of light under operation. For example, since the ambient light will vary when a user's eyelid blinks, the photoactive detector may record the response during a number, for example ten, signal periods between blink events. When the coloration mechanism changes the color, the average signal at the photoactive detector will concomitantly change and a signal may be sent to a controller within the biomedical device. In some examples, a light source may be included into the photodetector so that a calibrated light signal may pass through the coloration device and sense a change in absorbance in an appropriate spectral region. In some examples a quantitative or semi-quantitative detection result may result from irradiating the coloration device and measuring a photo-detection level at the photoactive detector and correlating that level to a concentration of the active coloration components.

Proceeding to FIGS. 7A and 7B, an alternative embodiment of an ophthalmic lens 700 with event coloration mechanisms 711-714, 721-724, and 731-734 is illustrated. In some such embodiments, the event mechanisms 711-714, 721-724, and 731-734 may include a reactive molecule 712-714, 722-724, and 732-734 respectively, anchored within the ophthalmic lens 700. The reactive molecule 712-714, and 732-734 may comprise a central binding portion 713, 733 flanked by a quencher 712, 732 and a coloration portion 714, 734, for example, a chromophore or fluorophore. Depending on the molecular structure, when a specified compound binds to the binding portion 713, 733, the coloration portion 714, 734 may shift closer to the quencher 712, reducing coloration, or may shift away from the quencher 732, which would increase coloration. In other embodiments, the reactive molecule 722-724 may comprise a binding portion 723 flanked by Förster resonance energy transfer (FRET) pairs 722, 724. FRET pairs 722, 724 may function similarly to a quencher 712, 732 and chromophore (the coloration portion) 714, 734, though FRET pairs 722, 724 may both exhibit coloration and, when in close proximity to each other, their spectral overlap may cause a change in coloration.

The reactive molecule 712-714, 722-724, and 732-734 may be selected to target specific compounds within the tear fluid. In some embodiments, the specific compound may directly indicate the event. For example, where a level of glucose in the tear fluid is the event, the reactive molecule 712-714, 722-724, and 732-734 may directly bind with the glucose. Where the event is the presence or concentration of a pathogen, for example, a particular aspect of that pathogen may bind with the reactive molecule 712-714, 722-724, and 732-734. This may include a unique lipid or protein component of that pathogen. Alternatively, the specific compound may be an indirect indicator of the event. The specific compound may be a byproduct of the pathogen, such as a particular antibody that responds to that pathogen.

Some exemplary target compounds may include: Hemoglobin; Troponi for the detection of myocardial events; Amylase for the detection of acute pancreatitis; creatinine for the detection of renal failure; gamma-glutamyl for the detection of biliary obstruction or cholestasis; pepsinogen for the detection of gastritis; cancer antigens for the detection of cancers; and other analytes known in the art to detect disease, injury, and the like.

In some embodiments, the reactive molecule 712-714 may be anchored within the ophthalmic lens 700 by a secondary compound 711, for example, a protein, peptide, or aptamer. Alternatively, the hydrogel 702 may provide a sufficient anchor to secure the reactive molecule 722-724 within the ophthalmic lens 700. The reactive molecule 722-724 may be in contact with the reactive monomer mix prior to polymerization, which may allow the reactive molecule 722-724 to chemically bind with the hydrogel 702. The reactive molecule may be injected into the hydrogel after polymerization but before hydration, which may allow precise placement of the reactive molecule.

In some embodiments, tinting the anchoring mechanism may provide broader cosmetic choices. The ophthalmic lens 700 may further comprise a limbic ring or an iris pattern, which may provide a static and natural background or foreground to the event coloration mechanisms. The design pattern may be included on or within the hydrogel or may be included in a rigid insert through a variety of processes, for example, printing on a surface of the rigid insert. In some such embodiments, the periphery event coloration mechanisms may be arranged to appear less artificial, for example through a sunburst pattern that may more naturally integrate into the wearer's iris pattern or an iris pattern included in the ophthalmic lens 700 than random dotting throughout the ophthalmic lens 700.

In other embodiments, the reactive molecule 732-734 may be anchored to a rigid insert 731. The rigid insert, not shown, may be annular and may anchor multiple reactive molecules outside of the optic zone 701. Alternatively, the rigid insert 731 may be a small periphery insert, which may anchor a single reactive molecule 732-734 or many of the same reactive molecules, which may allow for a more vibrant coloration.

As illustrated in cross section in FIG. 7B, the placement of the reactive molecules 760, 780 within the ophthalmic lens 750 may be varied within the hydrogel 752. For example, some reactive molecules 780 may be entirely in the periphery with no overlap with the optic zone 751. Other reactive molecules 760 may at least partially extend into the optic zone 751. In some such embodiments, the reactive molecules 760 may extend into the optic zone 751 in some configurations of that reactive molecule 760, such as when the event has occurred, which may alert the wearer of the event.

Further enablement for the use of fluorescence detectors in biomedical devices may be found as set forth in U.S. patent application Ser. No. 13/899,528 filed May 21, 2013, which is incorporated herein by reference.

Quantum-Dot Spectroscopy

Small spectroscopy devices may be of significant aid in creating biomedical devices with the capability of measuring and controlling concentrations of various analytes for a user. For example, the metrology of glucose may be used to control variations of the material in patients and after treatments with medicines of various kinds. Current microspectrometer designs mostly use interference filters and interferometric optics to measure spectral responses of mixtures that contain materials that absorb light. In some examples a spectrometer may be formed by creating an array composed of quantum-dots. A spectrometer based on quantum-dot arrays may measure a light spectrum based on the wavelength multiplexing principle. The wavelength multiplexing principle may be accomplished when multiple spectral bands are encoded and detected simultaneously with one filter element and one detector element, respectively. The array format may allow the process to be efficiently repeated many times using different filters with different encoding so that sufficient information is obtained to enable computational reconstruction of the target spectrum. An example may be illustrated by considering an array of light detectors such as that found in a CCD camera. The array of light sensitive devices may be useful to quantify the amount of light reaching each particular detector element in the CCD array. In a broadband spectrometer, a plurality, sometimes hundreds, of quantum-dot based filter elements are deployed such that each filter allows light to pass from certain spectral regions to one or a few CCD elements. An array of hundreds of such filters laid out such that an illumination light passed through a sample may proceed through the array of Quantum Dot (referred to as QD) Filters and on to a respective set of CCD elements for the QD filters. The simultaneous collection of spectrally encoded data may allow for a rapid analysis of a sample.

Figure 7C:
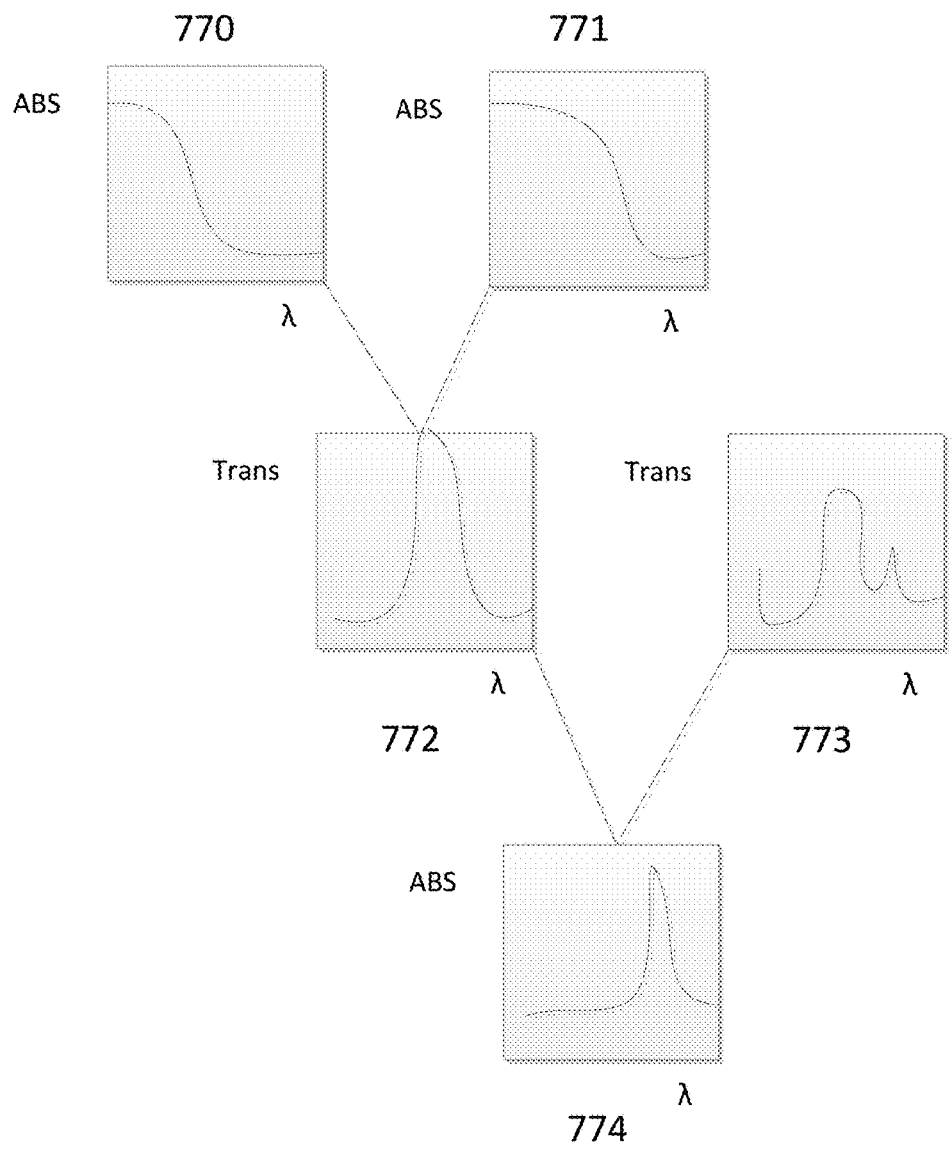
FIG. 7C illustrates how a spectral band may be analyzed with quantum-dot based filters.

Narrow band spectral analysis examples may be formed by using a smaller number of QD filters surrounding a narrow band. In FIG. 7C an illustration of how a spectral band may be observed by a combination of two filters is illustrated. It may also be clear that the array of hundreds of filters may be envisioned as a similar concept to that in FIG. 7C repeated may times.

In FIG. 7C, a first QD filter 770 may have an associated spectral absorption response as illustrated and indicated as ABS on the y-axis. A second QD filter 771 may have a shifted associated spectral absorption associated with a different nature of the quantum-dots included in the filter, for example the QDs may have a larger diameter in the QD filter 771. The difference curve of a flat irradiance of light of all wavelengths (white light) may result from the difference of the absorption result from light that traverses filter 771 and that traverses filter 770. Thus, the effect of irradiating through these two filters is that the difference curve would indicate spectral response in the depicted transmission band 772, where the y-axis is labelled Trans to indicate the response curve relates to transmission characteristics. When an analyte is introduced into the light path of the spectrometer, where the analyte has an absorption band in the UV/Visible spectrum, and possibly in the infrared, the result would be to modify the transmission of light in that spectral band as shown by spectrum 773. The difference from 772 to 773 results in an absorption spectrum 774 for the analyte in the region defined by the two quantum-dot filters. Therefore, a narrow spectral response may be obtained by a small number of filters. In some examples, redundant coverage by different filter types of the same spectral region may be employed to improve the signal to noise characteristics of the spectral result.

The absorption filters based on QDs may include QDs that have quenching molecules on their surfaces. These molecules may stop the QD from emitting light after it absorbs energy in appropriate frequency ranges. More generally, the QD filters may be formed from nanocrystals with radii smaller than the bulk exciton Bohr radius, which leads to quantum confinement of electronic charges. The size of the crystal is related to the constrained energy states of the nanocrystal and generally decreasing the crystal size has the effect of a stronger confinement. This stronger confinement affects the electronic states in the quantum-dot and results in an increased the effective bandgap, which results in shifting to the blue wavelengths both of both optical absorption and fluorescent emission. There have been many spectral limited sources defined for a wide array of quantum-dots that may be available for purchase or fabrication and may be incorporated into biomedical devices to act as filters. By deploying slightly modified QDs such as by changing the QD's size, shape and composition it may be possible to tune absorption spectra continuously and finely over wavelengths ranging from deep ultraviolet to mid-infrared. QDs can also be printed into very fine patterns.

Biomedical Devices with Quantum-Dot Spectrometers

Figure 8A:
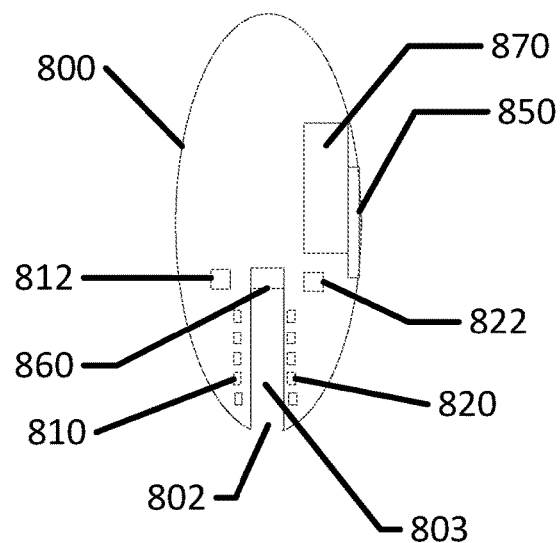
FIGS. 8A-8C illustrate an exemplary Quantum-Dot Spectrometer in a biomedical device.

FIG. 8A illustrates an exemplary QD spectrometer system in a biomedical device 800. The illustration in FIG. 8A may utilize a passive approach to collecting samples wherein a sample fluid passively enters a channel 802. The channel 802 may be internal to the biomedical device 800 in some examples and in other examples, as illustrated; the biomedical device 800 may surround an external region with a reentrant cavity. In some examples where the biomedical device 800 creates a channel of fluid external to itself, the device 800 may also contain a pore 860 to emit reagents or dyes to interact with the external fluid in the channel region. In a non-limiting sense, the passive sampling may be understood with reference to an example where the biomedical device 800 may be a swallowable pill. The pill may comprise regions that emit medicament 850 as well as regions that analyze surrounding fluid such as gastric fluid for the presence of an analyte, where the analyte may be the medicament for example. The pill may contain controller 870 regions proximate to the medicament where control of the release of the medicament may be made by portions of the biomedical pill device. An analysis region 803 may comprise a reentrant channel within the biomedical pill device that allows external fluid to passively flow in and out of the channel. When an analyte, for example in gastric fluid, diffuses or flows into the channel 802 it becomes located within the analysis region 803 as depicted in FIG. 8A.

Figures 8B, 8C:
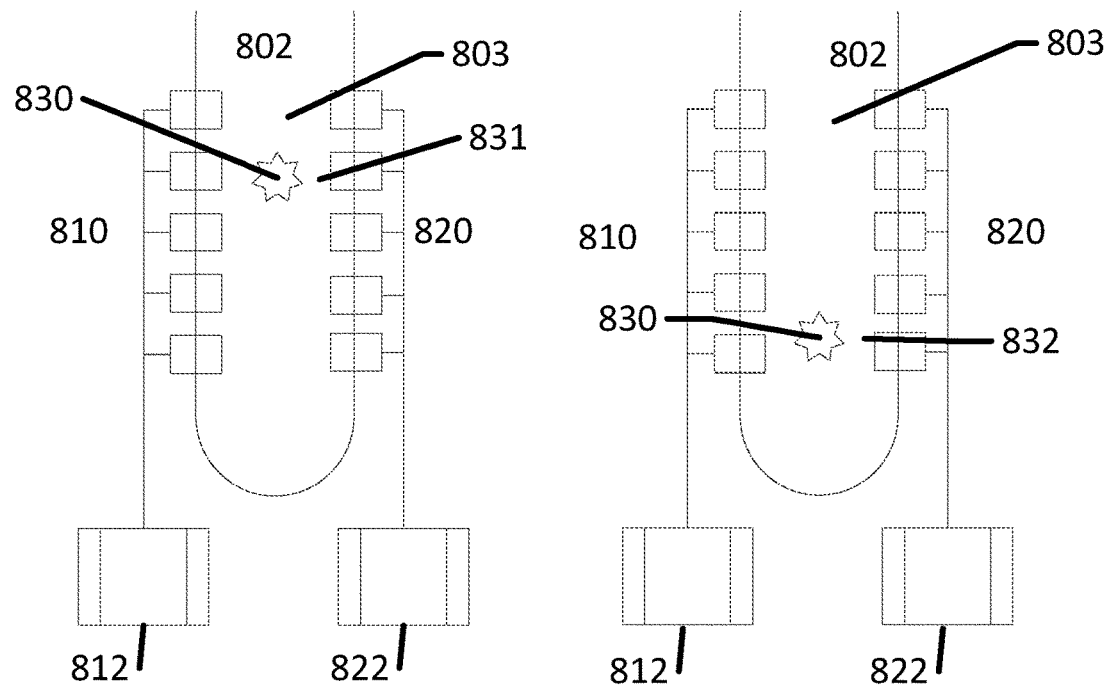

Referring now to FIG. 8B, once an analyte diffuses or otherwise enters the quantum-dot spectrometer channel which shall be referred to as the channel 802, a sample 830 may pass in the emission portion of a quantum-dot (QD) emitter 810. The QD emitters 810 may receive information from a QD emitter controller 812 instructing the QD emitters 810 to emit an output spectrum of light across the channel 802.

In some examples, the QD emitter 810 may act based on emission properties of the quantum-dots. In other examples, the QD emitter may act based on the absorption properties of the quantum-dots. In the examples utilizing the emission properties of the quantum-dots, these emissions may be photostimulated or electrically stimulated. In some examples of photostimulation; energetic light in the violet to ultraviolet may be emitted by a light source and absorbed in the quantum-dots. The excitation in the QD may relax by emitting photons of characteristic energies in a narrow band. As mentioned previously, the QDs may be engineered for the emission to occur at selected frequencies of interest. In a similar set of examples, QDs may be formed into a set of layers between electrically active layers that may donate electrons and holes into the QDs. These excitations, due to the donations of electrons and holes may similarly stimulate the QDs to emit characteristic photons of selected frequency. The QD emitter 810 may be formed by inclusion of nanoscopic crystals, that function as the quantum-dots, where the crystals may be controlled in their growth and material that are used to form them before they are included upon the emitter element.

In an alternative set of examples, where the QDs act in an absorption mode a combination of a set of filters may be used to determine a spectral response in a region. This mechanism is described in a prior section in reference to FIG. 7C. Combinations of QD absorption elements may be used in analysis to select regions of the spectrum for analysis.

In either of these types of emission examples, a spectrum of light frequencies may be emitted by QD emitter 810 and may pass thru the sample 830. The sample 830 may absorb light from some of the emitted frequencies if a chemical constituent within the sample is capable of absorbing these frequencies. The remaining frequencies that are not absorbed may continue on to the detector element, where QD receivers 820 may absorb the photons and convert them to electrical signals. These electrical signals may be converted to digital information by a QD detector sensor 822. In some examples the sensor 822 may be connected to each of the QD receivers 820, or in other examples the electrical signals may be routed to centralized electrical circuits for the sensing. The digital data may be used in analyzing the sample 830 based on pre-determined values for QD wavelength absorbance values.

In FIG. 8C, the QD system is depicted in a manner where the sample is passed in front of spectral analysis elements that are spatially located. This may be accomplished, for example, in the manners described for the microfluidic progression. In other examples, the sample 830 may contain analytes that diffuse inside an region of a biomedical device that encloses external fluid with material of the biomedical device to form a pore or cavity into which the sample may passively flow or diffuse to an analytical region that passes light from emitters within the biomedical device, outside the biomedical device, and again to detectors within the biomedical device. FIGS. 8B and 8C depict such movement as the difference between the locations of the sample 830 which has moved from a first location 831 along the analysis region to the new location 832. In other examples the QDs may be consolidated to act in a single multidot location where the excitation means and the sensing means are consolidated into single elements for each function. Some biomedical devices such as ophthalmic devices may have space limitations for a spectrometer comprising more than a hundred quantum-dot devices, but other biomedical devices may have hundreds of quantum-dot devices which allow for a full spectrographic characterization of analyte containing mixtures.

The QD analytical system may also function with microfluidic devices to react samples containing analytes with reagents containing dyes. The dye molecules may react with specific analytes. As mentioned previously, an example of such a binding may be the FRET indicators. The dye molecules may have absorption bands in the ultraviolet and visible spectrum that are significantly strong, which may also be referred to as having high extinction coefficients. Therefore, small amounts of a particular analyte may be selectively bound to molecules that absorb significantly at a spectral frequency, which may be focused on by the QD analytical system. The enhanced signal of the dye complex may allow for more precise quantification of analyte concentration.

In some examples, a microfluidic processing system may mix an analyte sample with a reagent comprising a dye that will bind to a target analyte. The microfluidic processing system may mix the two samples together for a period that would ensure sufficient complexing between the dye and the analyte. Thereafter, in some examples, the microfluidic processing system may move the mixed liquid sample to a location containing a surface that may bind to any uncomplexed dye molecules. When the microfluidic system then further moves the sample mixture into an analysis region, the remaining dye molecules will be correlatable to the concentration of the analyte in the sample. The mixture may be moved in front of either quantum-dot emission light sources or quantum-dot absorption filters in the manners described.

A type of fluorescent dye may be formed by complexing quantum-dots with quenching molecules. A reagent mixture of quantum-dots with complexed quenching molecules may be introduced into a sample containing analytes, for example in a microfluidic cell, within a biomedical device. The quenching molecules may contain regions that may bind to analytes selectively and in so doing may separate the quenching molecule from the quantum-dot. The uncomplexed quantum-dot may now fluoresce in the presence of excitation radiation. In some examples, combinations of quantum-dot filters may be used to create the ability to detect the presence of enhanced emission at wavelengths characteristic of the uncomplexed quantum-dot. In other examples, other manners of detecting the enhanced emission of the uncomplexed quantum-dots may be utilized. A solution of complexed quantum-dots may be stored within a microfluidic processing cell of a biomedical device and may be used to detect the presence of analytes from a user in samples that are introduced into the biomedical device.

Ophthalmic Insert Devices and Ophthalmic Devices with Microfluidic Detectors

Figure 9A:
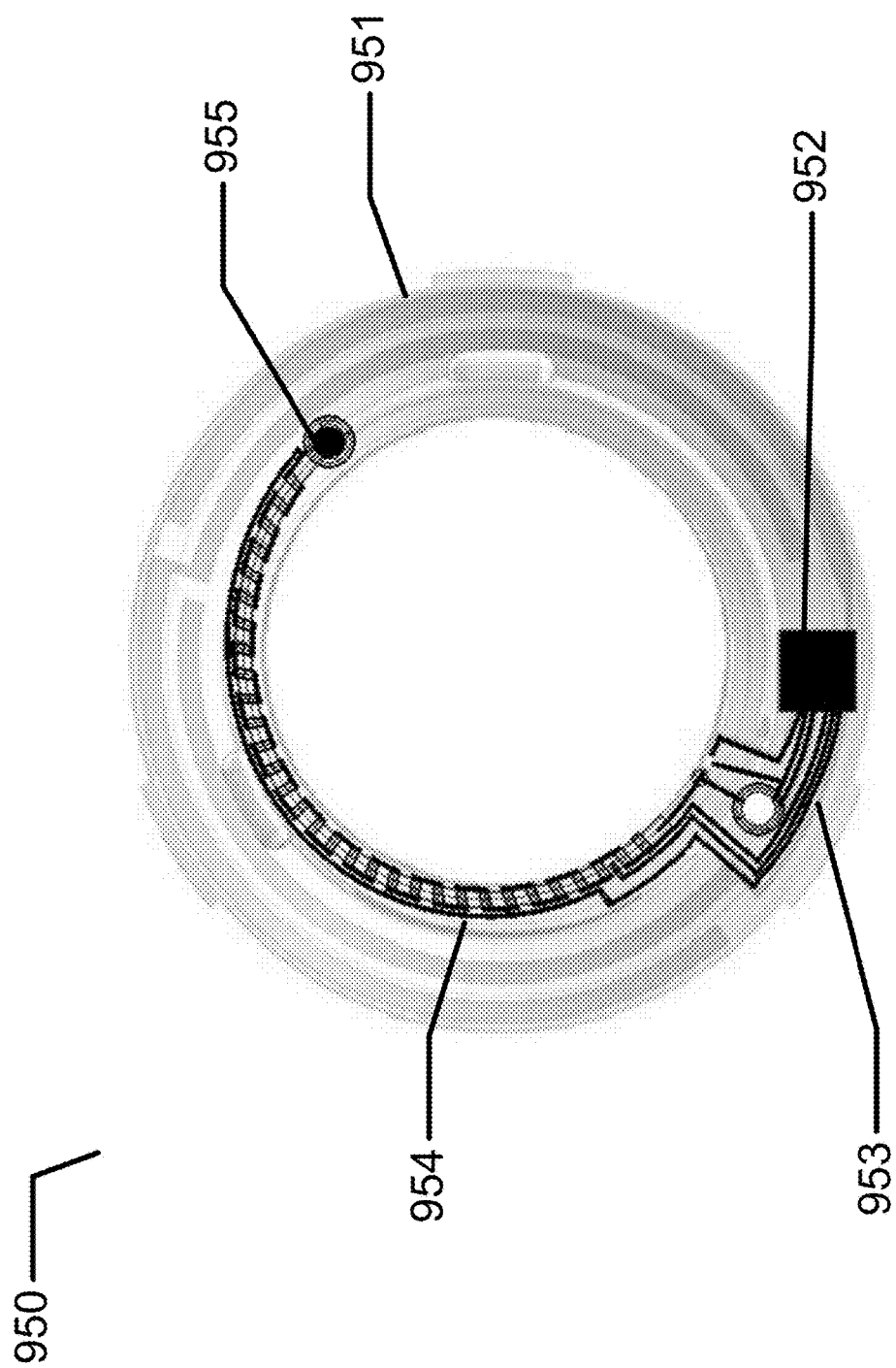
FIG. 9A illustrates an exemplary microfluidic based biometric monitoring device.

Referring now to FIG. 9A, a top view of an exemplary microfluidic analytical system 950 of an ophthalmic device is depicted upon an ophthalmic media insert. In addition to energization elements 951, control circuitry 952, and interconnect features 953, in some embodiments, the media insert may include microfluidic analytical components 954 including a waste fluid retention component 955. The microfluidic analytical system 950 may be capable of determining an analyte/biomarker, in terms of its presence or its concentration, in a fluid sample. A microfluidic analytical system may chemically detect numerous analytes that may be found in a user's tear fluid. A non-limiting example may include detection of an amount of glucose present in a sample of tear fluid.

Further enablement for the use of fluorescence detectors in biomedical devices may be found as set forth in U.S. patent application Ser. No. 13/896,708 filed May 17, 2013, which is incorporated herein by reference.

Figure 9B:
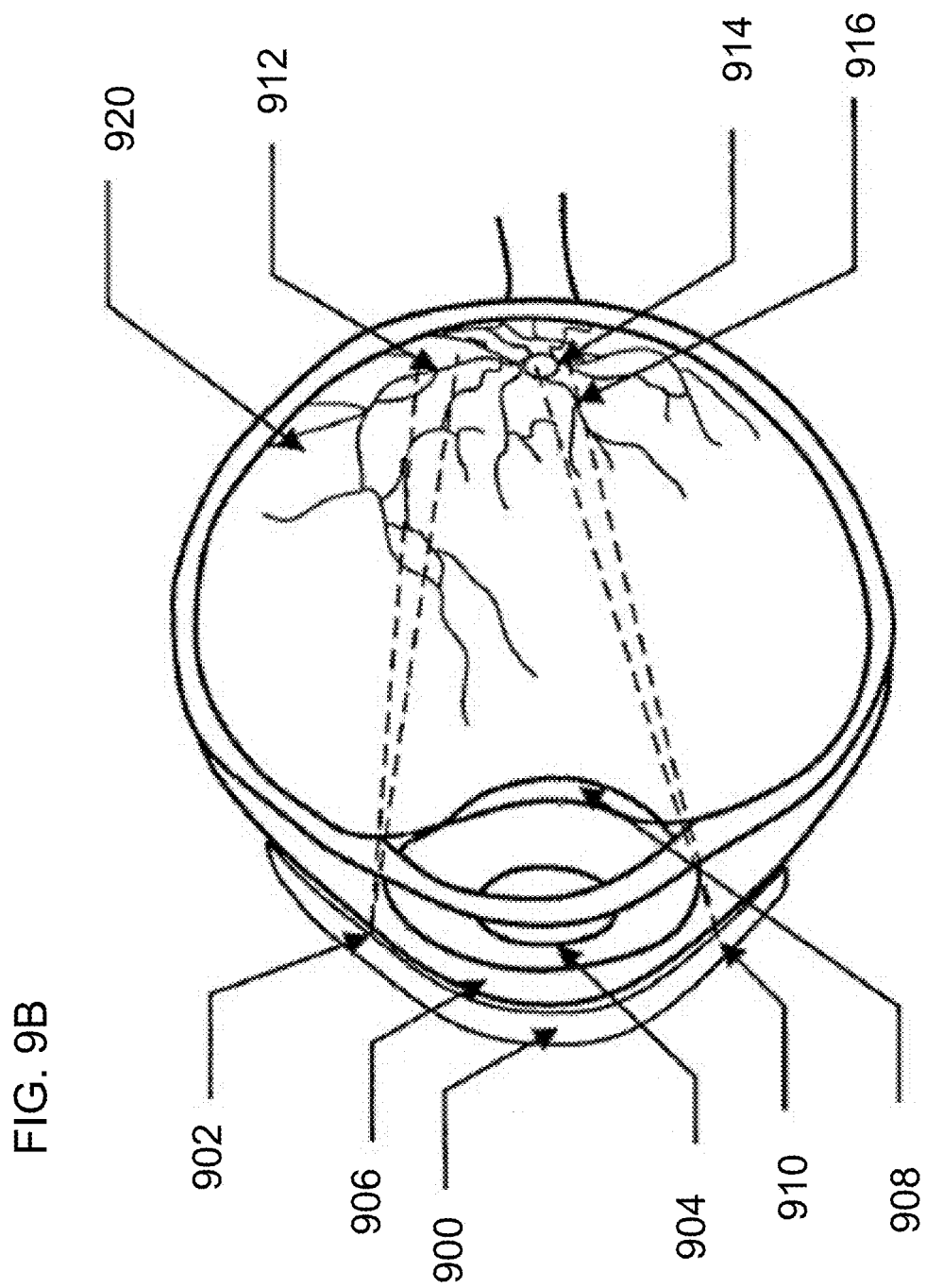
FIG. 9B illustrates an exemplary retinal vascularization based biometric monitoring device.

Ophthalmic Insert Devices and Ophthalmic Devices with Retinal Vascularization Detectors Referring now to FIG. 9B, a side cross section representation of a patient's eye with an exemplary energized ophthalmic device is illustrated. In particular, an ophthalmic device 900 taking the form of an energized contact lens is illustrated resting on the cornea 906 with ocular fluid in at least some portions between the ophthalmic device 900 and the cornea 906. In some embodiments, the concave contour of the ophthalmic device 900 may be designed so that one or more piezoelectric transducers can rest directly on the cornea 906. Having the piezoelectric transducers resting directly on the cornea 906 may allow greater imaging detail as ultrasonic pulses can travel directly towards the cornea 906 from focal points 902, 910. As depicted in the present exemplary embodiment, the piezoelectric transducer(s) are located on the peripheral area of the energized contact lens and outside of the line of sight to prevent interference with vision. However, in alternative energized contact lens devices the piezoelectric transducer may be located in the center region located in front of the pupil 904 also without significantly interfering with the vision of a user.

Accordingly, depending on the design of the ophthalmic device 900 the ultrasonic pulses may pass through the eye's crystalline lens 908 before passing through the vitreous humour 920 and reaching one or more retinal areas including pulsating vessels, e.g. 912 and 916. In some embodiments, the retinal areas may be pre-determined areas near or that include ocular parts serving a specific function or that can be used as a predictor of a particular condition including, for example, the macula 914 which may be screened for the early detection of peripheral vision loss. The detected electrical signal may also provide a data stream related to the users pulse and blood pressure as non-limiting examples.

Further enablement for the use of ultrasonic pulse based detectors in biomedical devices may be found as set forth in U.S. patent application Ser. No. 14/087,315 filed Nov. 22, 2013, which is incorporated herein by reference.

Location Awareness

Location awareness may be very important for biometric based information communication embodiments. There may be numerous manners to establish location awareness. In some examples a biomedical device may function in cooperation with another device such as a smart phone. There may be a communication link established between the biomedical device and the other device. In such embodiments, the device such as the smart phone may perform the function of determining the location of the user. In other examples, the biomedical device may be used in a standalone manner and may have the ability to determine location. In a standalone manner, the biomedical device may have a communication means to interact with a computer network. There may be many ways to connect to networks and other network accessible devices including in a non-limiting sense Wi-Fi communication, cellular communication, Bluetooth communication, ZigBee communication and the like. Connections to networks may be used to determine location. Location may be estimated based on the known location of a network access device which may be accessed by the biomedical device or its associated device such as a smartphone. Combinations of network access devices or cellular access devices may allow for triangulation and improved location determination.

In other examples, the biomedical device or its associated device may directly determine its own location. These devices may have radio systems that may interact with the global positioning system network (GPS). The receipt of a number of signals from satellites may be processed and algorithms used in standardized manners to determine a location of the GPS radio with a close accuracy.

By determining a location for the user to a certain degree of geographic accuracy various location based information communication embodiments may be enabled.

Biometrics

Biometrics specifically means the measurement of biologically relevant aspects. In common usage the term has come to mean the measurement of biological aspects of an individual that may be utilized for identification or security aspects such as finger prints, facial characteristics, body type and gait as examples. As used herein, biometrics refers more generally to biological characteristics that may be measured or analyzed with a biomedical device. In later sections of this description numerous examples of useful biometric data for the purpose of biometric based information communication are disclosed. The biometric parameter of temperature may be a non-limiting example. There may be numerous means to measure temperature on the surface of a user and in the core of a user. The measurement of temperature may show a deviation from normal. The measurement may be coupled with other information about the location of the user and the current ambient temperature may be obtained. If the biometric core temperature is low and the ambient temperature is also low, the user may be directed to options for preferred warm beverages or clothing. On the other hand, high temperatures may direct towards preferred cold beverage suppliers or clothing. A generalized trend towards a higher temperature unrelated to an ambient temperature rise may cause the biometric based information communication system to enquire whether a local doctor or pharmacy may be desired by a user. There may be numerous information communication uses for measurements of such biometric data.

Figure 10:
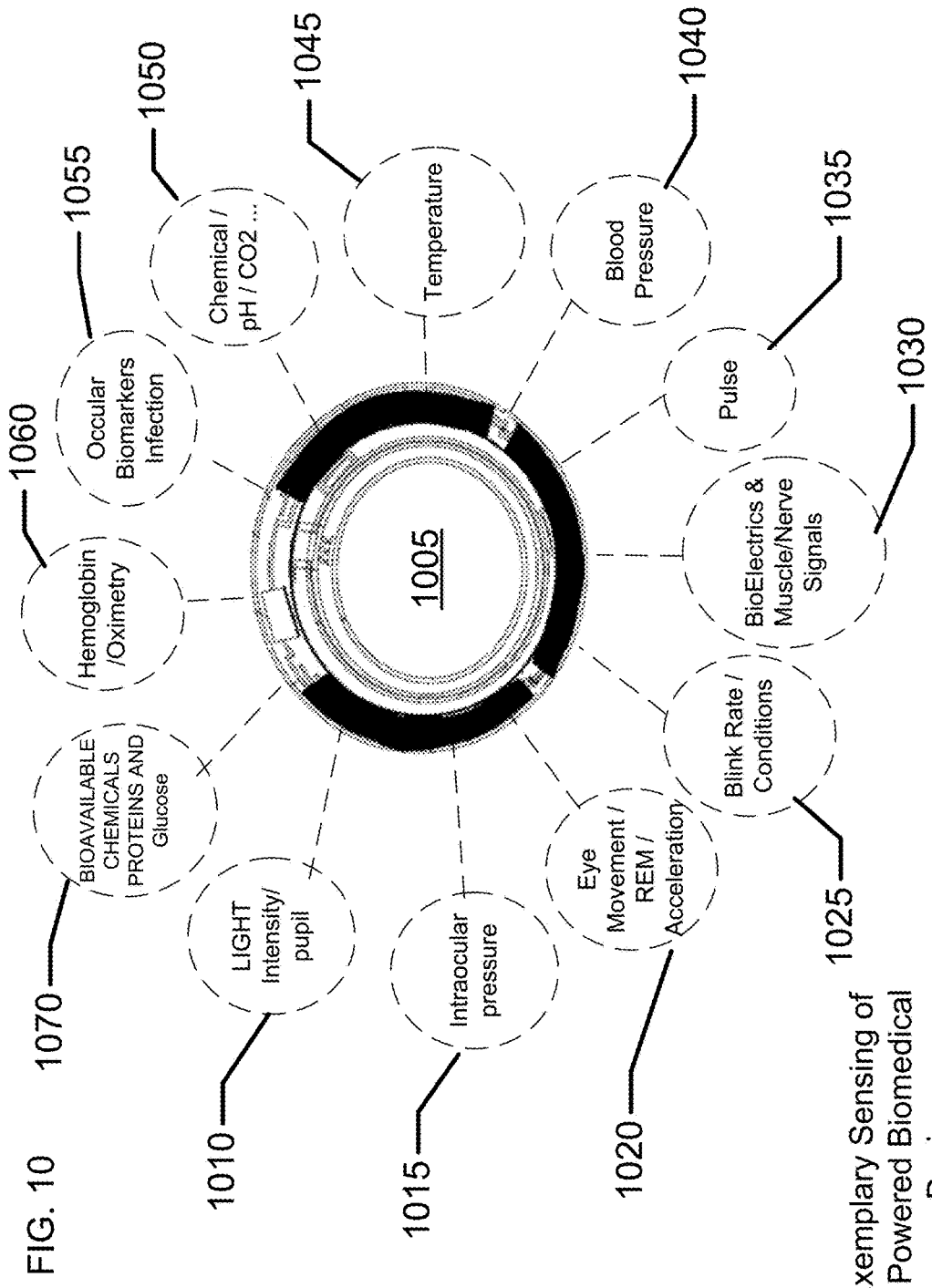
FIG. 10 illustrates an exemplary display system within a biomedical device.

Referring to FIG. 10 examples of some biometric data that may be obtained through an exemplary ophthalmic biomedical device type 1005, for example, an electronic ophthalmic lens is found. In some examples an ophthalmic device may be able to measure and/or analyze one or more of the following types of biometric data. In some examples, an ophthalmic device may be able to detect and measure characteristics of a pupil in concert with an ambient light level 1010. Further enablement for measuring pupil characteristics may be found in U.S. patent application Ser. No. 13/780,135 filed Feb. 28, 2013, which is incorporated by reference herein.

In another example an ophthalmic device may be able to measure or estimate an intraocular pressure 1015. Further enablement for the measurement of intraocular pressure in biomedical devices may be found as set forth in U.S. patent application Ser. No. 14/087,217 filed Nov. 22, 2013, which is incorporated herein by reference.

In another example an ophthalmic device may be able to measure or estimate movement of a user's eye 1020 by, for example, mems based accelerometers incorporated into an ophthalmic lens. There may be numerous purposes for measuring eye movement such as the estimation of the sleep status of the user. In some examples, it may be unsafe for a user to be sleeping and applications may take action on such a measurement and determination. In other examples, sleep status of the user may be assessed during rapid eye movement (REM) sleep states. The time and duration of rem sleep of a user may allow an information communication system to suggest doctors, sleep aids, nutritionals and the like. Further enablement for measuring rem sleep may be found in U.S. patent application Ser. Nos. 13/780,074 and 13/780,479 both filed Feb. 28, 2013, which are incorporated by reference herein.

In another example, an ophthalmic device may be able to measure or estimate characteristics of a user's blink function 1025. There may be numerous environmental or health conditions which may be correlated to the blink function and a biometric based information communication system may suggest products or services related to the condition. In a simplified example a combination of users blink function 1025 and characteristics of a pupil in concert with an ambient light level may evoke information communication options for various types of sun glasses. Further enablement for measuring blinking may be found in U.S. patent application Ser. Nos. 13/780,607 and 13/780,014 both filed Feb. 28, 2013, which are incorporated by reference herein.

In another example, an ophthalmic device may be able to measure or estimate characteristics of the bioelectric signals and muscle/nerve signaling 1030. In some examples, the ophthalmic device may include antennas or other wireless means to sense electrical signals in the environment of the ophthalmic device. In other examples, biologically consistent materials may protrude from the ophthalmic device where the materials may be electrically conductive. The protrusions may be capable of measuring electric signals directly. The sensed electrical signals may be amplified and conferred to the processing elements of the ophthalmic device to associate functional meaning to the signals.

In another example, an ophthalmic device may be able to measure or estimate characteristics of the user's pulse 1035. In some examples, pressure sensitive elements may register a pressure wave as an electrical signal. Piezoelectric and electroactive polymer sensors may provide a non-limiting example of sensing which may register pressure waves as electrical signals that may be processed with processing elements within the device. In other examples, light signals may be focused upon regions of the ophthalmic environment which include blood vessels upon a surface region. In some examples, changes in scattering characteristics of the light upon reflection provide the necessary means to extract a blood pulse signal.

In another example, an ophthalmic device may be able to measure or estimate characteristics of a user's blood pressure 1040 or relative blood pressure. In some examples, the sensing capabilities that measure blood pressure may be calibrated to determinations of the relative pressure that is occurring within the vessels or the ophthalmic environment itself. In other examples, imaging elements may be able to image vessels to determine the relative change in shape and size during heart beats which may be correlated to relative pressure changes in the user.

In another example, an ophthalmic device may be able to measure or estimate characteristics of a user's temperature 1045. In some examples, infrared detectors may sense levels of infrared light within a user's eyeball by focusing into the environment. A blink detector may be used to sense the time period during which a user's eyelid may be closed where levels of infrared light may be more limited to sources internal to the eye environment and therefore more closely correlated to the body temperature. In other examples, direct probes within the ophthalmic device may sense temperatures of the eye tissues that it contacts directly. In some examples, the contact measurement may correlate a resistance value or a thermocouple voltage value to a sensed temperature.

In another example, an ophthalmic device may be able to measure or estimate chemical characteristics of a user's eye 1050. The chemical characteristics may relate to levels of $CO_2$ in the users blood or tissues, pH of tear fluid and the like. In some examples, a pH level may be estimated based on sampling fluids in the environment of the ophthalmic device into the device and measuring the pH via colorimetric techniques of indicators or by electrical measurements of microsized electrode pairs which may be correlated to pH measurements. Other chemical characteristics may be determined by introducing samples into processing regions of the ophthalmic device for colorimetric, spectroscopy or electrical characterization in manners such as have been previously described herein. In similar manners for another example, an ophthalmic device may be able to measure or estimate ocular characteristics and biomarkers for the presence of an infection 1055.

In another example, an ophthalmic device may be able to measure or estimate characteristics of a user's hemoglobin and levels of oximetry of the user's blood 1060. In some examples, a combination of wavelengths of light may be reflected from internal surfaces of a user's eye when looking inward or to reflection from the eyelid when looking outwards. The relative absorption characteristics at these wavelengths may be correlated to oximetry levels in the blood streams probed by the light. In some examples, the detected signals may be correlated to pulsation for improved detection.

In still another example, an ophthalmic device may be able to measure or estimate the presence and concentration of bioavailable chemicals and proteins 1070. As a non-limiting example, the level of glucose in tear fluid may be assessed, or a level of glucose in intercellular regions such as in the sclera may be assessed. In some examples, estimates of significant divergence may cause a biometric system to suggest a medical treatment option; whereas, for smaller divergence from normal readings a user may be suggested a food product or service in the vicinity of the user.

There may be numerous other examples of biometric readings that may be obtained and used in a biometric information communication system. Responses from an information communication and health perspective may be expected to evolve and become more numerous and sophisticated with time and experience; however, the methods and devices discussed herein provide the backbone and basic solutions for obtaining biometric data and communication and processing such data to enable the using of such data in an information communication perspective.

Figure 11:
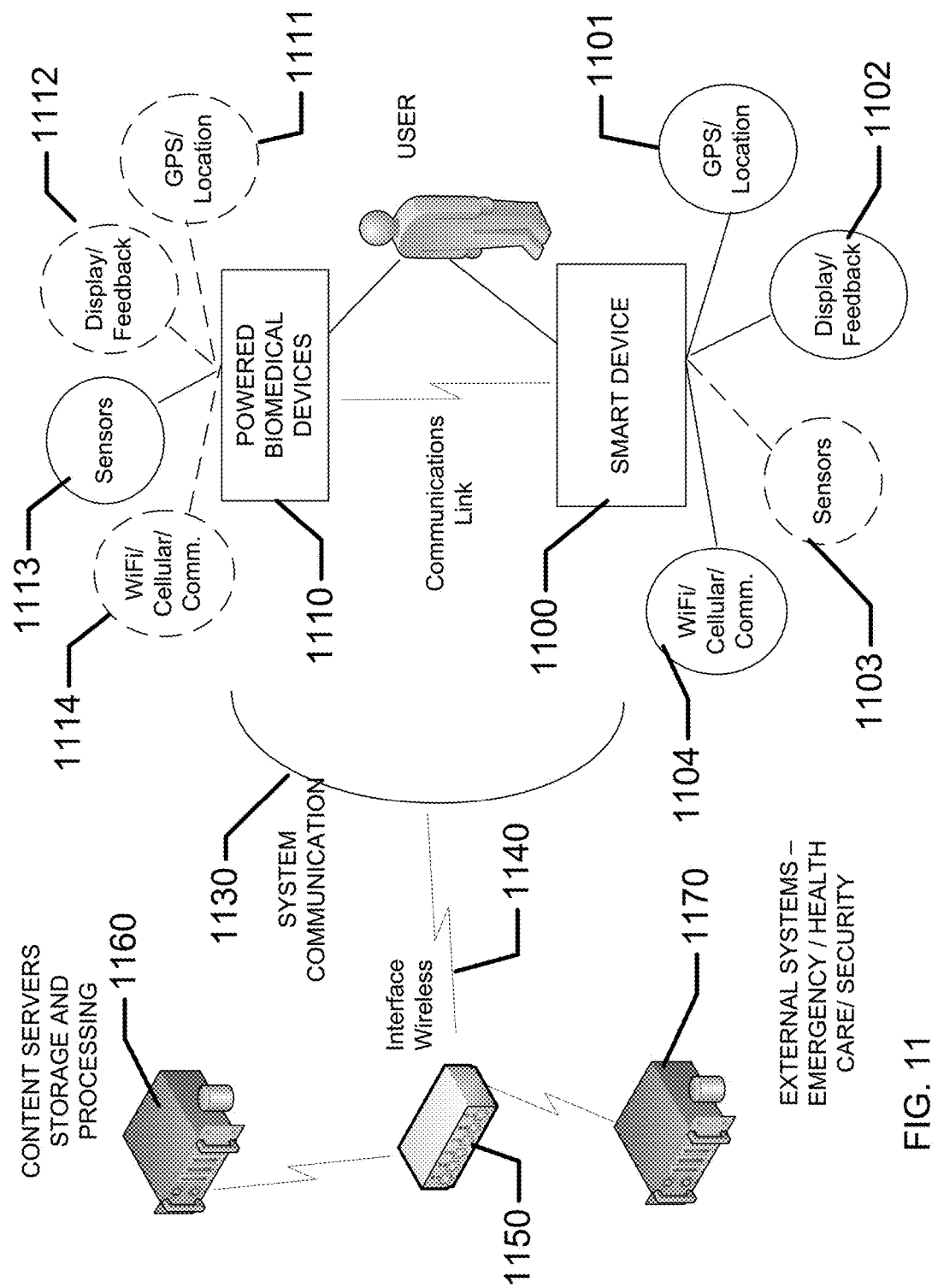
FIG. 11 illustrates an exemplary network of biomedical, user and data processing devices consistent with the concepts of biometric based information communication focused on some exemplary functionality of the biomedical device.

Functional and Operational Schema for Biomedical Devices in Biometric Based Information Communication Referring now to FIG. 11, an exemplary operational schema for a biometric based biomedical device in a biometric based information communication system is illustrated. In the illustrated example, a user has in his or her possession a powered biomedical device 1110 and a related smart device 1100. These two devices may exchange information and data and otherwise communicates with each other. In these examples, the powered biomedical device 1110 may have one or more biometric devices and sensors 1113 operational. In some examples, the biomedical device 1110 may also have (depicted as dotted lines in the illustration to convey that some examples may not have the function) a display/feedback element 1112 which may include audio, vibrational and other means of feedback. The biomedical device 1110 may also have a GPS or location capability 1111 and a Wi-Fi or cellular communication capability 1114. In some cases, the communication capability may be based on another standard such as Bluetooth or ZigBee or may operate on a customized communication protocol and system. In cases where a powered biomedical device pairs with another smart device it may be practical for the powered biomedical device 1110 to provide functionality for basic communication with the smart device as well as to function for acquisition of one or more types of biometric data.

The paired device to the biomedical device 1110, that is the smart device 1100, may therefore have a complement of functions. In reality, the smart device 1100 may have enhanced power storage capabilities to a biomedical device 1110 and therefore this may improve the device's capability for computation, communication, display and other functions. The smart device may have a Wi-Fi/cellular communication capability 1104, a GPS or location sensitivity capability 1101, and a display/feedback capability 1102 which may include audio, vibrational and other means of feedback. Even though the biomedical device may have a significant function for the acquisition of biometric data, the smart device 1100 may nonetheless have functional sensors 1103 of various kinds which may be redundant to those in the biomedical device, may be complementary to those in the biomedical device or may relate to sensing that is not of a biometric data perspective.

The combination of the powered biomedical device 1110 and smart device 1100 each connected to a user may operate as a system and may have a unified communication protocol for system communication 1130. In many examples, the smart device 1100 may provide the major functionality for the system communication 1130, and may operate wireless communication capability 1140 to a network access device 1150. The network access device 1150 may be a device such as a Wi-Fi network hub or a cellular communications hub. In either event the network access device 1150 may provide the communication pathway to route data from the biometric information communication system to various external systems such as, in non-limiting examples, content servers, storage and processing systems 1160 that may mediate and operate connection to various information. In addition the network access device may provide the communication pathway to external systems for emergency and healthcare related systems 1170 for information communication or emergency related activity.

Biomedical Device Display

In some examples the biomedical device may have a display function. In some examples, a display function within an ophthalmic device may be limited to an LED or a small number of LEDs of different color that may provide a display function to alert a user to look at another paired device for a purpose. The purpose may have some encoding based on the color of the LED that is activated. In more sophisticated examples, the display may be able to project images upon a user's retina. In a biometric based information communication system, the display of imagery may have obvious utility based upon standard information communication approaches based on imagery. In the examples as have been provided, a measurement of a biometric data set may therefore; trigger an exchange of data via the various communications means and a targeted visual communication may be communicated to the biomedical device and then displayed via a biomedical device display.

Figure 12:
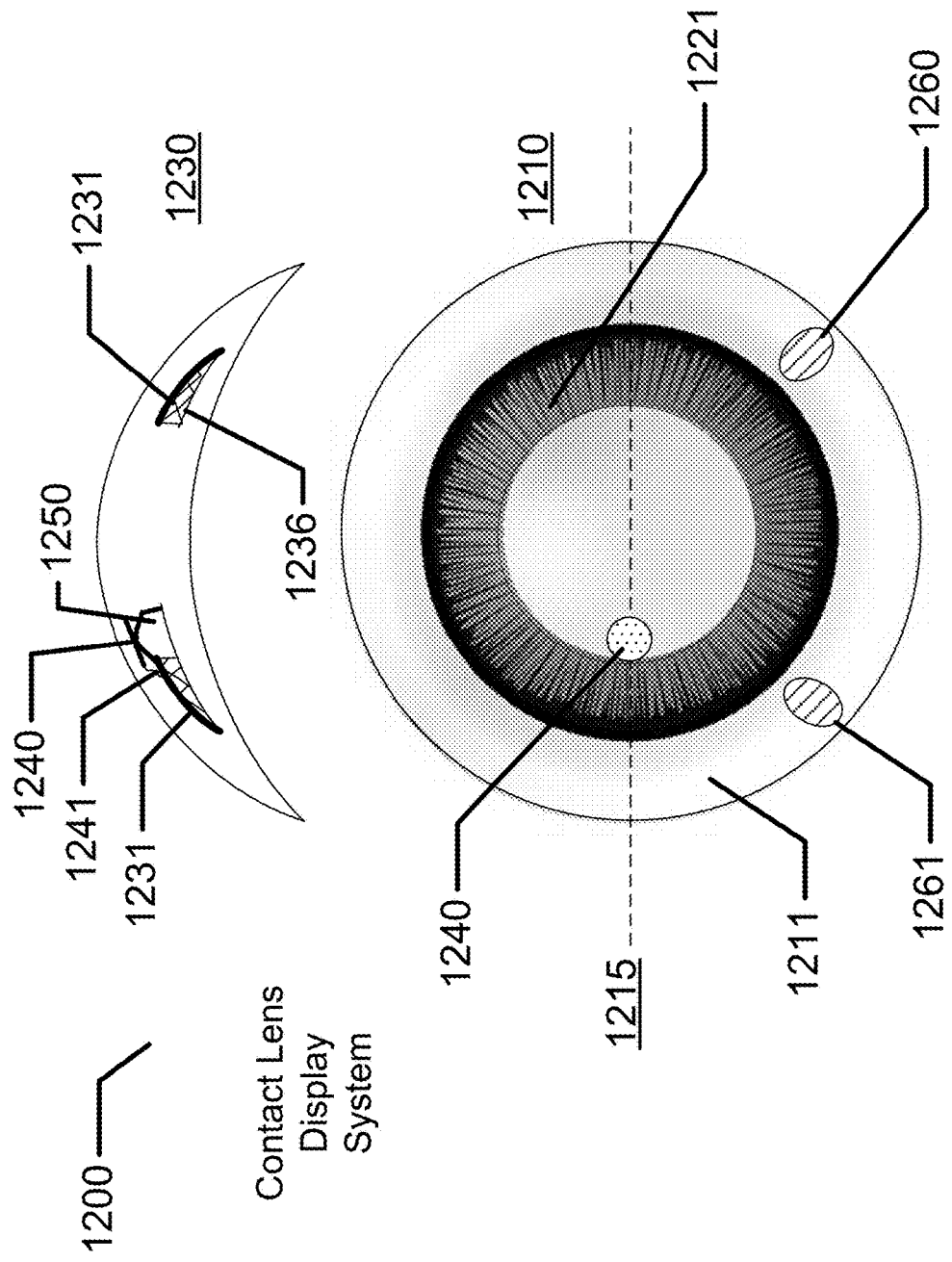
FIG. 12 illustrates exemplary sensing mechanisms that may be performed by an ophthalmic based biometric monitoring device.

Now referring to FIG. 12, a display within an exemplary biomedical device 1200 is illustrated. Item 1210 may be an ophthalmic device capable of being worn on a user's eye surface. It may be formed of a hydrogel-based skirt 1211 that completely surrounds in some embodiments, or partially surrounds or supports an insert device in other embodiments. In the depiction, the skirt 1211 surrounds a fundamentally annular insert device 1236. Sealed within the insert device 1236 may be energization elements, electronic circuitry for control, activation, communication, processing and the like. The energization elements may be single use battery elements or rechargeable elements along with power control systems, which enable the recharging of the device. The components may be located in the insert device as discrete components or as stacked integrated devices with multiple active layers as described above. These components are discussed in detail above.

The ophthalmic device may have structural and cosmetic aspects to it including, stabilization elements 1260 and 1261 which may be useful for defining orientation of the device upon the user's eye and for centering the device appropriately. The fundamentally annular device may have patterns printed upon one or more of its surfaces depicted as an iris pattern item 1221 and in the cross section 1230, along the line 1215, as items 1231.

The insert device 1236 may have a photonic-based imaging system in a small region of the optical zone as shown as item 1240. In some examples a 64×64 pixel imaging system may be formed with a size roughly of 0.5 mm×0.5 mm. In cross section, it may be observed that item 1240 may be a photonic projection component that may comprise photonic emitter elements; an EWOD based pixel transmittance control device, a light source or multiple light sources and electronics to control these components. The photonic-based imaging system may be attached to a lens system 1250 and be connected to the annular insert component by a data and power interconnection bus 1241.

In some embodiments, the lens system may be formed of static lens components that focus the near field image of the imaging system to a fixed location in space related to the body of the ophthalmic device. In other embodiments, the lens system may also include active components. For example, a meniscus based lens device with multiple electrode regions may be used to both translate the center of the projected image and adjust the focal power of the device to adjust the focus and effectively the size of the image projected. The lens device may have its own control electronics or alternatively it may be controlled and powered by either the photonic-based imaging component or the annular insert device or both.

In some embodiments, the display may be a 64×64 pixel based projection system, but more or less pixels are easily within the scope of the inventive art, which may be limited by the size of the pixel elements and the ophthalmic device itself. The display may be useful for displaying dot matrix textual data, image data or video data. The lens system may be used to expand the effective pixel size of the display in some embodiments by rastering the projection system across the user's eye while displaying data. The display may be monochromatic in nature or alternatively have a color range based on multiple light sources. Data to be displayed may be communicated to the ophthalmic lens from an outside source, or data may originate from the ophthalmic device itself from sensors, or memory components for example. In some cases data may originate both from external sources with communication and from within the ophthalmic device itself.

Further enablement for the use of display devices in biomedical devices may be found as set forth in U.S. patent application Ser. No. 13/842,009 filed Mar. 15, 2013, which is incorporated herein by reference.

Biometric Based Personalized Information Communication

Various aspects of the technology described herein are generally directed to systems, methods, and computer-readable storage media for providing personalized content. Personalized content, as used herein, may refer to advertisements, organic information, promotional content, or any other type of information that is desired to be directed to a user. The personalized content may be provided by, for example, a target content provider, such as an advertising provider, an informational provider, etc. Utilizing embodiments of the present invention, the user or a content provider may select specific content that it would like to target. The relevant information may be detected by the device, and communicated through various communication systems to a system that can analyze the status and provide appropriate content. Once analyzed, the personalized content may then be presented to the user by the system. In some examples, the biomedical device may present the content to the user or in other examples; a paired device may present the content.

In an example, personalized content may be presented, for example, as real time visual content on an ophthalmic lens, audio content transmitted to the user through a biomedical device, or a target content may be an experience on a secondary companion device such as a cell-phone, tablet, or computer.

Calls for Medical Attention

In the general operation of a biometric based information communication system, information may be presented to a user based on the data produced by the biometric information communication system. The biometric data may be supplemented by data related to the location and/or environment of the user. However, in some examples, there may be a set of biometric data conditions where the logical analysis of the data may be a severe health condition. Under such circumstances, the biometric based information communication system may call out to emergency services or other medical attention to assist the user. As the system has control of the biometric data and may have data relating to location. This information may also be forwarded with the communication to emergency services or other medical attention.

Security Measures

Biometric data may support the various functions of a biometric information communication system as have been described. However, biometric data may have confidential and legal significance. Therefore, the biomedical device and other devices along the communication sequence may encrypt the biometric data before transmission so that any interception by a third party may not result in a meaningful result. There may be numerous means to ensure the security of biometric data consistent with the apparatus and methods of biometric based information communication systems as presented herein. Encryption methods for data are well known in the relevant art.

Methods

Figure 13:
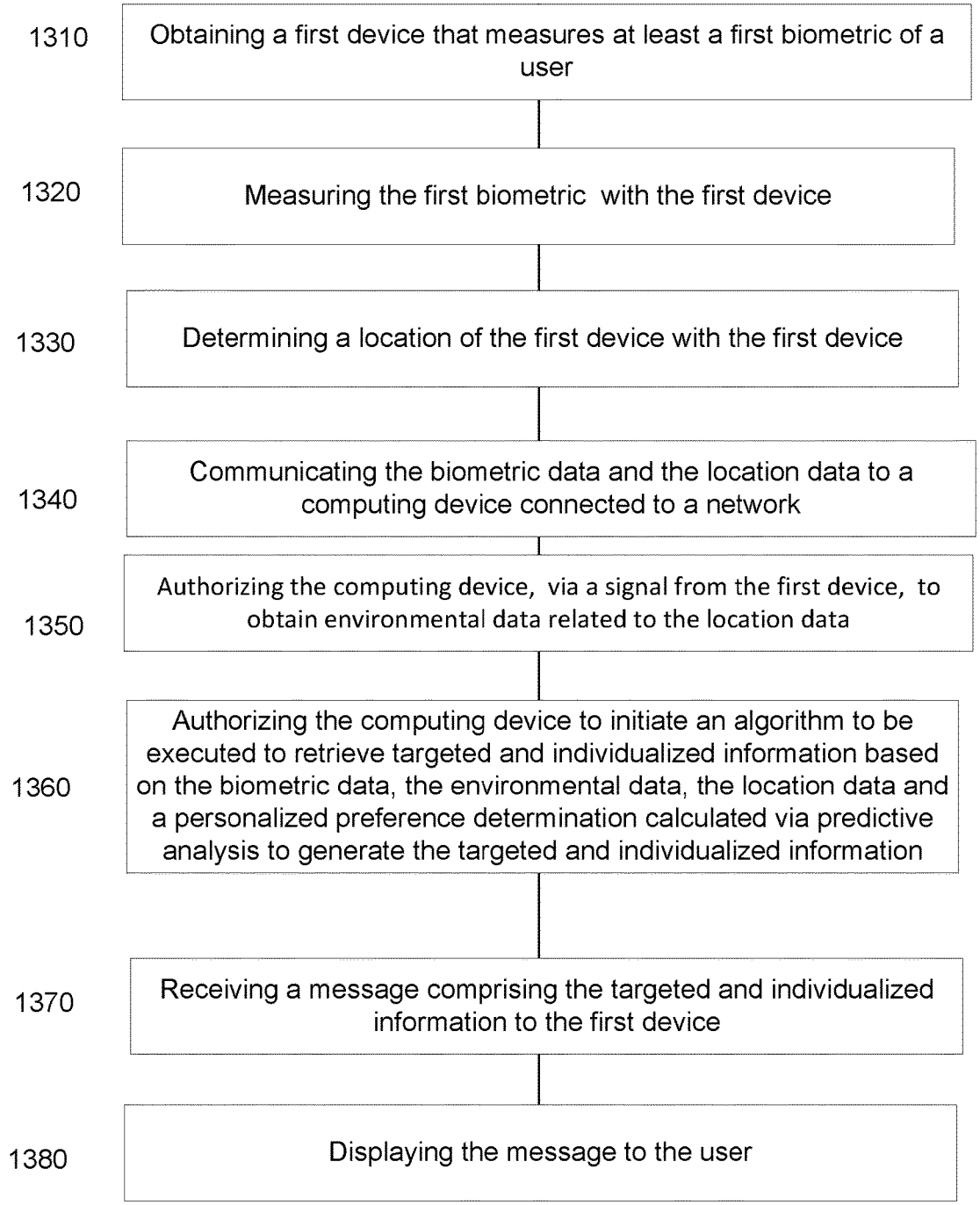
FIG. 13 illustrates an exemplary process flow diagram for biometric based information communication.

Referring to FIG. 13 a flow chart of an exemplary method for a biometric based information communication process is displayed. At 1310 the method may start by obtaining a first device, wherein the device measures at least a first biometric of a user. Next at 1320, the method continues by measuring the first biometric with the first device. Next at 1330, the method continues by determining the user's geographic location. Next at 1340, the method continues by communicating the biometric data and the location data to a computing device connected to a network. Next at 1350, the method continues by authorizing the computing device, via a signal from the first device, to obtain environmental data related to the location data. Next at 1360, the method continues by authorizing the computing device to initiate an algorithm to be executed to retrieve targeted and individualized content based on the biometric data, the environmental data, the location data and a personalized preference determination calculated via predictive analysis to generate the targeted and individualized content. Next at 1370, the method continues by receiving a message comprising the targeted and individualized content to the first device. And, at 1380 the method continues by displaying the message to the user. There may be many such methods where additional steps are performed and where the order of specific steps may be altered.

Figure 14:
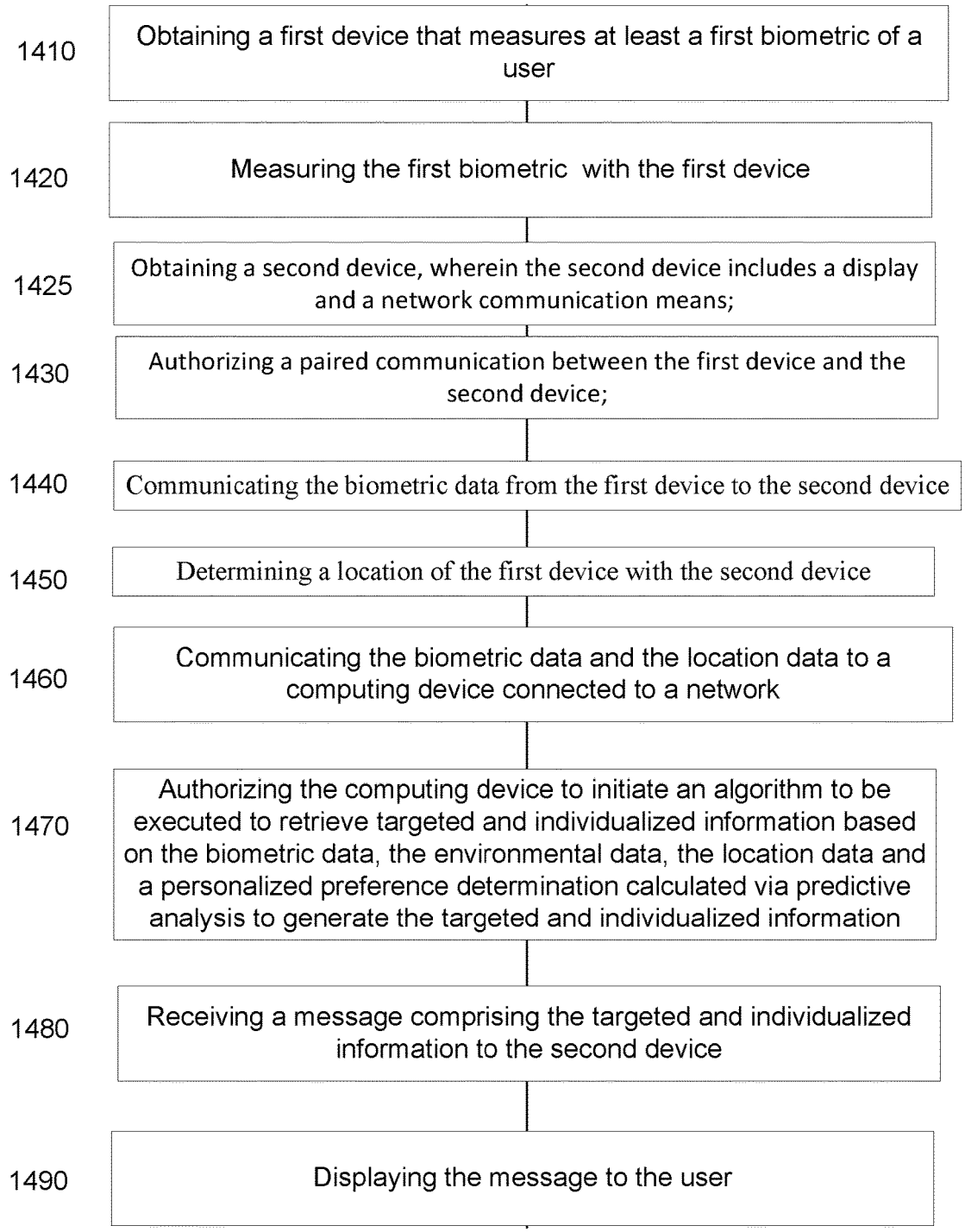
FIG. 14 illustrates an additional exemplary process flow diagram for biometric based information communication.

Referring to FIG. 14 a flow chart of an exemplary method for a biometric based information communication process is displayed. At 1410, the method may start by obtaining a first device, wherein the device measures at least a first biometric of a user. Next, at 1420 the method continues, and the first device is used to measure the previously mentioned first biometric. At 1425, the method proceeds by obtaining a second device, wherein the second device includes a display and a network communication means. Next at 1430 the method continues by authorizing a paired communication between the first device and the second device. At 1440, a method step of communicating the biometric data from the first device to the second device may occur. Next at 1450, the method continues by determining a location of the first device with the second device. Next at 1460, the method proceeds by communicating the biometric data and the location data to a computing device connected to a network; authorizing the computing device, via a signal from the first device, to obtain environmental data related to the location data. At 1470, the method continues by authorizing the computing device to initiate an algorithm to be executed to retrieve targeted and individualized content based on the biometric data, the environmental data, the location data and a personalized preference determination calculated via predictive analysis to generate the targeted and individualized content. Continuing at 1480 the method may include receiving a message comprising the targeted and individualized content to the second device; and at 1490 displaying the message to the user. There may be many such methods where additional steps are performed and where the order of specific steps may be altered.

Figure 15:
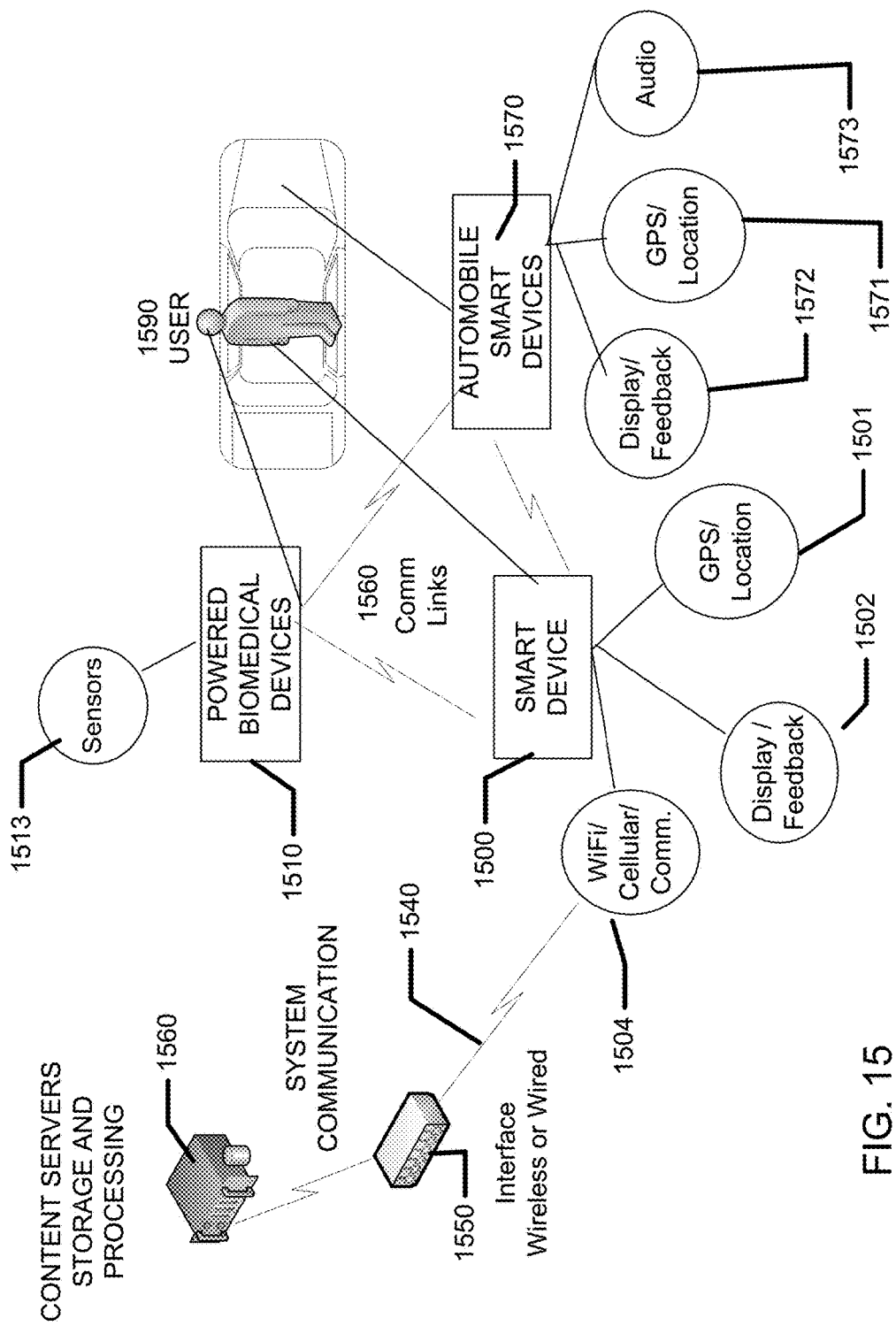
FIG. 15 illustrates an exemplary process flow diagram for biometric based information communication including an automotive device and an automotive smart device.

Referring now to FIG. 15, an exemplary operational schema for a biometric based biomedical device in a biometric based information communication system utilized within an automobile is illustrated. In the illustrated example, a user has in his or her possession a powered biomedical device 1510 and a related smart device 1500, where the user and both devices are placed inside of an automobile 1590 that also has smart device capabilities 1570. These two devices 1510 and 1500 and the automobile 1590 may exchange information and data and otherwise communicate with each other via communication links to content and storage and processing providers 1560. In these examples, the powered biomedical device may have one or more biometric devices and sensors 1513 operational. In some cases, the communication capability may be based on another standard such as Bluetooth or ZigBee or may operate on a customized communication protocol and system. In cases where a powered biomedical device 1510 pairs with another smart device 1500 or automobile smart devices 1570 it may be practical for the powered biomedical device to provide functionality for basic communication with the smart device as well as to function for acquisition of one or more types of biometric data.

The paired smart device 1500 to the biomedical device 1510 may therefore have a complement of functions in a suggested optional or included perspective. In reality, the smart device 1500 may have enhanced power storage capabilities to a biomedical device 1510 and therefore this may improve the device's capability for computation, communication, display and other functions. The smart device 1500 may have a Wi-Fi/cellular communication capability 1504, a GPS or location sensitivity capability 1501, and a display capability 1502. Even though the biomedical device 1510 may have a significant function for the acquisition of biometric data, the smart device 1500 may nonetheless have functional sensors of various kinds which may be redundant to those in the biomedical device, may be complementary to those in the biomedical device or may relate to sensing that is not of a biometric data perspective.

Similarly, the paired automobile smart device 1570 to the biomedical device 1510 may also have a complement of functions in a suggested optional or included perspective. In some examples, the automobile smart device 1570 may have enhanced power storage capabilities to a biomedical device 1510 and, therefore, this may improve the device's capability for computation, communication, display and other functions. The automobile smart device 1570 may have a GPS or location sensitivity capability 1571, a display capability 1572, and an audio feedback device 1573. Even though the biomedical device 1510 may have a significant function for the acquisition of biometric data, the automobile smart device 1500 may nonetheless have functional sensors of various kinds which may be redundant to those in the biomedical device, may be complementary to those in the biomedical device or may relate to sensing that is not of a biometric data perspective.

The combination of the powered biomedical device 1510, smart device 1500, and automobile smart device 1570 each in an automobile connected to a user 1590 may operate as a system and may have a unified communication protocol for system communication 1540. In this example, the smart device 1500 may provide the major functionality for the system communication 1540, and may operate wireless communication capability 1540 to a network access device

1550. The network access device 1550 may be a device such as a Wi-Fi network hub or a cellular communications hub. In either event the network access device 1550 may provide the communication pathway to route data from the biometric information communication system to various external systems such as, in non-limiting examples, content and storage and processing systems 1560 that may mediate and operate connection to information communication information.

This device may be worn by a user who is driving in a motor vehicle, such as a car, truck, or motorcycle, among other examples. This biomedical device may be paired with the user's smartphone with GPS capabilities, and both may be connected to the vehicle and may convey information to the user visually with the screen or verbally with the vehicle's speaker system. Communication with the user may be possible with the screen of the phone, as well as its speakers, however due to the dangers involved with using a smartphone while operating a vehicle; it may be desired to facilitate this communication with the vehicle's systems for safety reasons. The biomedical device may be used to collect biometric data from the user; as a non-limiting example, the device may be used as a glucose monitor to collect data on the user's blood sugar levels. The biomedical device may detect that the user has low blood sugar when in the vehicle; it may communicate this information to the user via the communication capabilities through the vehicle. In doing so, using location based tracking systems, the user may be recommended food options in their area, that they may be used to raise their low blood sugar levels. In some examples, the biometric data value may be used to initiate communication to the content, storage and processing systems and the information that may be conveyed to the user may be tailored based on algorithmic analysis of the user's preferences. In some examples, such a preference may be based on previous experience the user may have had in some options in the region. In still further examples, the content system may correlate various aspects of the user and the biometric data and offer information to the user that may relate to improved control of glucose levels, exercise programs, specialized medical providers and other such examples.

In some examples, the user may also be recommended drink options in their area, that when consumed may raise their low blood sugar, as another non-limiting example. If a user's blood sugar level may be found to be significantly low or high, the user may be warned and given information concerning nearby medical facilities. In this case, the biomedical device may access the user's contact list, and may send alerts to certain recipients, as may be possible for the user to determine, to warn the user's contact list that the user is in trouble, and may need help. In these cases, specific information, such as the user's location, may also be sent to the user's contact list, among other possible pieces of information. In the event of an adverse occasion such as a vehicle accident, the sensor information may be conveyed, in some examples, to allow for optimized medical intervention. In some examples, the biometric sensing of glucose may detect an elevated level and provide information to the user in the various means as have been described to alert the user to the condition.

Figure 16:
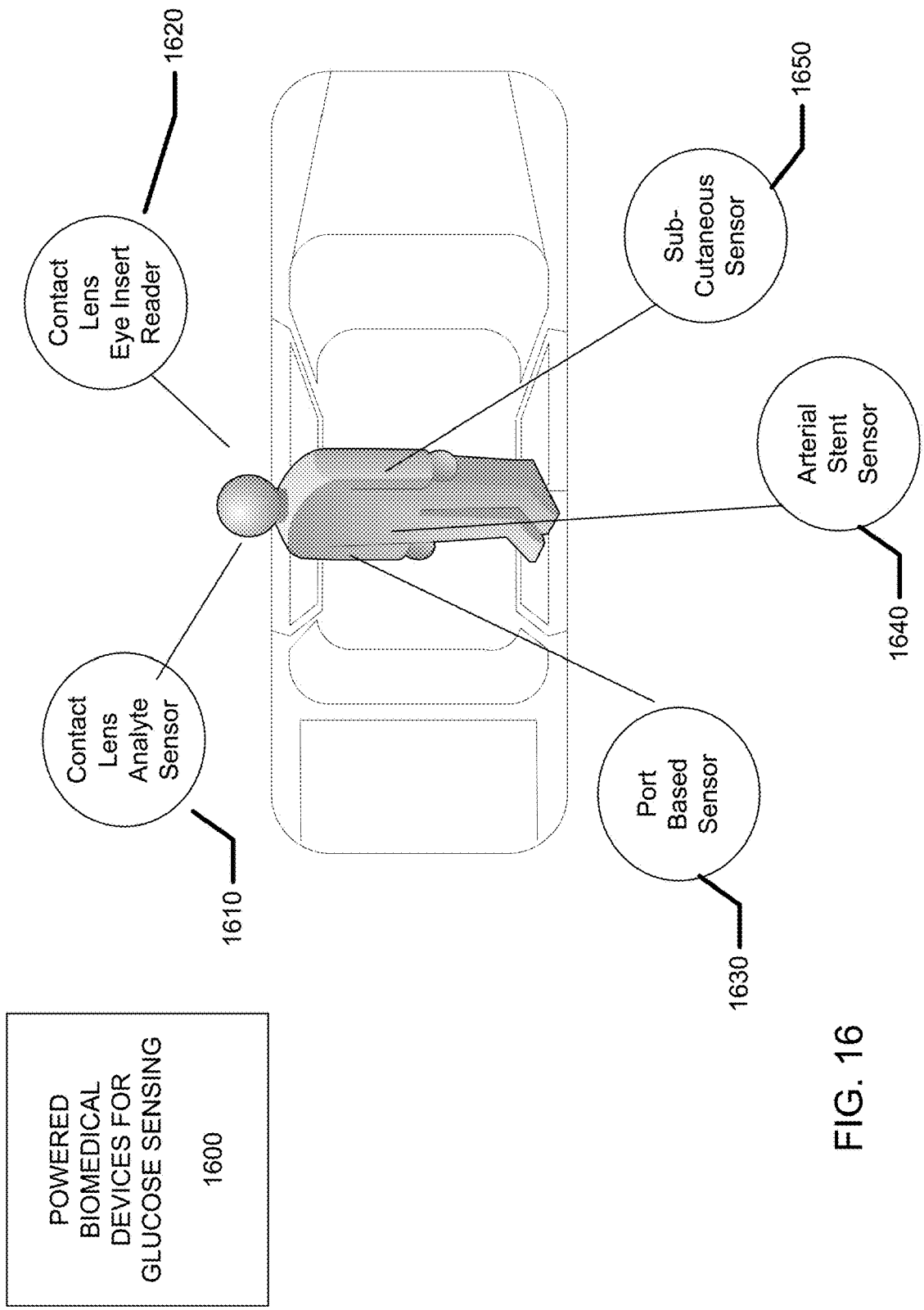
FIG. 16 illustrates examples of devices for glucose sensing that may be used for biometric based information communication.

Referring to FIG. 16, multiple examples of a powered biomedical device for glucose sensing may include a contact lens analyte sensor 1610, a contact lens eye insert reader 1620, a vascular port based sensor 1630, an arterial stent sensor 1640, or a sub-cutaneous sensor 1650. One or more of these examples may be utilized in a biometric based information communication system configured within an automobile, as described in FIG. 15.

An example of a powered biomedical device for glucose sensing 1600 may include the contact lens analyte sensor 1610. This device may include, for example, a hydrogel contact lens to be placed on a user's eye. This device may have sensing electronics and components contained within the hydrogel lens. This device may also have energization elements and electronic components contained within the hydrogel lens. In some examples, the electronics may be contained within an insert device. The sensing electronics of this device may sample and analyze a user's tear fluid to detect the presence and quantities of analytes. The device may function to detect various types of analytes via Forester Resonance Energy Transfer (FRET). In some examples, the analyte may bind to FRET probes on the sensor, which may cause a measurable change in the fluorescent emission of the fluorophores in the probes. The changes in these emissions may be sensitive to glucose concentration, thus allowing them to yield a measure of glucose concentration.

Another example of a powered biomedical device for glucose sensing may include a contact lens based eye insert reader 1620. An eye insert may include a hydrogel that encapsulates a FRET based glucose sensitive molecule. The insert may be a small hydrogel insert that may be surgically placed within a user's eye. The insert may last for roughly a year inside the eye, and may possess the probes used for FRET, where the FRET based molecules may be entrapped in the hydrogel matrix while the glucose analyte in aqueous interstitial solution may be free to diffuse about the hydrogel matrix. The reading device may include, for example, a shaped hydrogel contact lens with alignment features and a flap designed to overlap with the location of the eye insert. The contact lens based reader device may have sensing electronics and components that photo-actively excite the FRET molecules. Another portion of the contact lens based reader may comprise a detector element that may be sensitive to fluorescence signals that may emit from the FRET molecules. This device may function to detect various types of analytes via FRET, in these examples the focus may be Glucose.

Another example of a powered biomedical device for glucose sensing 1600 may include a vascular port based sensor 1630. In typical applications, a user may have a vascular port device surgically implanted in their body to aid in receiving regular intravenous injections. Similar devices may be configured to function as a powered biomedical device for glucose sensing 1600. The vascular port device installed in the user may be installed with a vascular port based sensor 1630, as this device may be in regular contact with the user's blood to allow for regular biometric sensing of the user's blood. This device may have sensing electronics and components contained within. This device may also have energization elements, as well as other electronic components contained within. This device may function to detect various types of analytes via FRET or quantum dot based spectroscopy; as this device may be in direct contact with the user's blood, changes in the user's blood chemistry may be sensed as they happen.

Another example of a powered biomedical device for glucose sensing 1600 may include an arterial stent sensor 1640. In typical applications, a user may have a stent surgically implanted in their body to aid in solving medical arterial issues. In other applications a similar device may function as a powered biomedical device for glucose sensing 1600. The stent installed in the user may be installed with an arterial stent sensor 1630, as this device may be in regular contact with the user's blood to allow for regular biometric sensing of the user's blood. This device may have sensing electronics and components contained within. This device may also have energization elements, as well as other electronic components also contained within. This device may function to detect various types of analytes via FRET, quantum dot spectroscopy and other analysis devices. Since this stent device may be in direct contact with the user's blood, changes in the user's blood chemistry may be sensed as they happen.

In some examples, a powered biomedical device for glucose sensing 1600 may include a subcutaneous sensor 1640. This device may consist of a casing resistant to the buildup of biofilm, and may have sensing electronics and components contained within. The device may be inserted below a user's skin surface. This device may also have energization elements, as well as other electronic components and analyte sensing components contained within. This device may function to detect various types of analytes via FRET, quantum dot spectroscopy and other analysis techniques; as this device may be in direct contact with the user's interstitial fluid, changes sensed by the biomedical device result from those analytes that may be exchanged from the user's blood system and the interstitial fluid at the rate that such analytes diffuse into the proximity of the subcutaneous sensor 1640.

Figure 17:
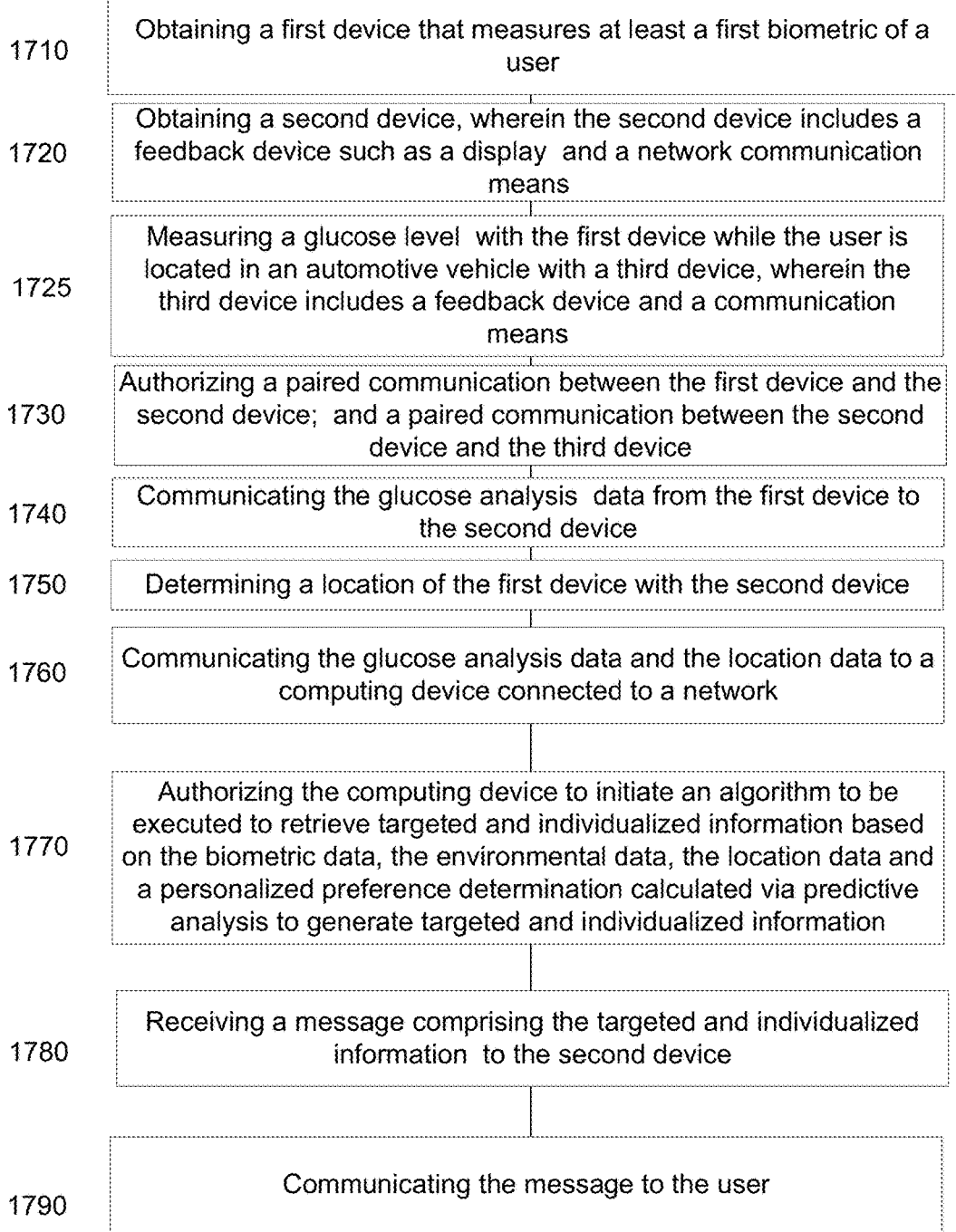
FIG. 17 illustrates an exemplary process flow diagram for glucose sensing based biometric based information communication.

Referring to FIG. 17, a flow chart of a method for communicating information based on the obtaining of a biometric analysis result may be obtained. At 1710 the method may start by obtaining a first device, wherein the device measures at least a first biometric of a user. Next at 1720, the method continues by obtaining a second device, wherein the second device includes a feedback device such as a display and a network communication means. Next at 1725 the method may continue by measuring a glucose level with the first device while the user is located in an automotive vehicle with a third device, wherein the third device includes a feedback device and a communication means. Next at 1730, the method continues by authorizing a paired communication between the first device and the second device; and a paired communication between the second device and the third device. Next at 1740, the method may continue by communicating the glucose analysis data to the second device. Next at 1750, the method may continue by determining a location of the first device with the second device. Next at 1760 the method may continue by communicating the glucose analysis data and the location data to a computing device connected to a network. Next at 1770, the method continues by authorizing the computing device to initiate an algorithm to be executed to retrieve targeted and individualized information based on the biometric data, the environmental data, the location data and a personalized preference determination calculated via predictive analysis to generate targeted and individualized information. Next at 1780, the method continues by receiving a message comprising the targeted and individualized information to the second device. Next at 1790 the message may be communicated to the user. In some examples, the communication to the user may be made through devices in the automobile. In an example, the display screen in an automobile media center may visually display a message. The visual display may include text, images, and combinations of text and imagery. The information displayed may be incorporated into a navigation display such as a map where a location related to a text or an image may be displayed. In some examples, the message may also be converted into an audio message in the form of verbal communication or as sounds. In some examples, the message may engage a vibration creating device that may be located in the driver seat of the automobile. In some examples, a message may be conveyed via a dashboard display. In some examples a message may be conveyed via a heads up display on the windshield of the device. There may be numerous means that a message may be conveyed to a user. In some examples, the second device may be used to convey a message related to the biometric data result. In still further examples, the first device used to measure a biometric may as well include means to convey a message and it may be used to convey the message herein. Combination of some or all of these communication means may be employed in some examples. There may be many such methods where additional steps are performed and where the order of specific steps may be altered.

Sensing Examples

Figure 18:
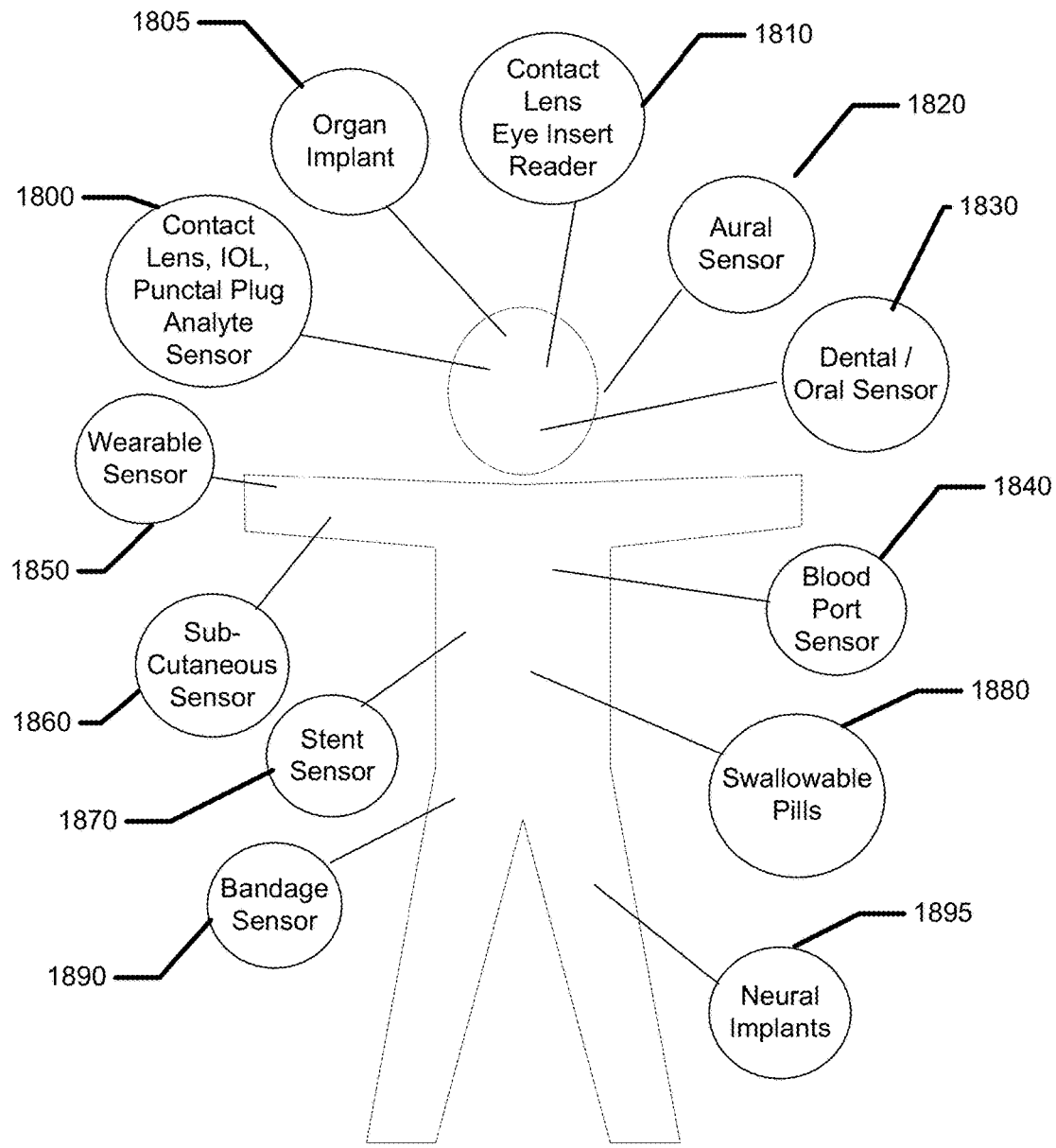
FIG. 18 illustrates various exemplary sensing devices in accordance with the present invention.

There may be numerous types of biomedical related sensing techniques that may be used individually or in combinations to perform sensing consistent with the present invention. Referring to FIG. 18, a summary of numerous exemplary types of biomedical devices may be found. The various ophthalmic devices 1800, such as contact lenses, intraocular devices, punctal plugs and the like, some of which have been described in detail herein may perform various sensing functions including analyzing analytes in the biofluids in the ocular environment.

Contact lenses, 1810 may also be used to read and quantify results from sensing devices that may be implanted into ocular tissue as has been previously mentioned herein.

Implants into organs 1805, may include brain implants, heart implants, pacemakers, and other implants that are implanted into organs of the user. These implants may be able to directly sense or indirectly sense a user's cellular tissue layer or a fluid contacting a user's cellular tissue layer.

In other examples, a biomedical sensing device may be an aural sensor 1820. The aural sensor may indirectly sense a biometric such as temperature as an infrared signal for example. The aural sensor may also be able to quantify other biometrics such as blood oxygenation, analyte and bio-organism sensing and other such sensing.

A dental sensor 1830 may be used to sense a variety of different types of biometric data. The sensor may probe the fluids in the oral cavity for biomolecules and chemical species from food, and the biological fluids in the environment. The sensor may also probe for indirect measurements of various types including in a non-limiting perspective pressures, temperatures, flows and sounds in the environment that may be directly or indirectly related to biometrics such as body temperatures, breathing rates, durations, strengths and the like.

Vascular port sensors 1840 may be used to sense various aspects within a blood stream. Some examples may include glucose monitoring, oxygen monitoring or other chemical monitoring. Other biometrics may be monitor at a vascular port such as blood pressure or pulse as non-limiting examples.

Some biometric sensors may be wearable sensors 1850. A wearable sensor 1850 may indirectly measure a variety of biometrics. In some examples, the sensing element may be independent of any body tissue or body fluid of a user. Such a sensing element may monitor biometrics related to the user's body as a whole, such as the amount of motion the user. Other wearable sensors may directly or indirectly sense or probe a user's cellular tissue layer which may allow measurements of temperature, oxygenation, and chemical analysis of perspiration as non-limiting examples. The wearable sensors 1850 may take the form of or be incorporated into clothing or jewelry in some examples. In other examples the wearable sensors 1850 may attach to clothing or jewelry.

Various examples of biometric sensors may be incorporated into sub-cutaneous sensors 1860 where a surgical procedure may place a biomedical device with sensors beneath a skin layer of a user. The sub-cutaneous sensor 1860 may be sensitive with direct contact to tissue layers or to interstitial fluids. The sub-cutaneous sensor 1860 may be able to analyze for various analytes, such as for example with techniques described previously herein. Physical parameters may also be measured such as temperature, pressure and other such physically relevant biometric parameters.

Sensors may be incorporated into blood vessel or gastrointestinal stents of various kinds forming stent sensor 1870. The stent sensors 1870 may therefore be able to perform sensing of various chemical species. Stent sensors 1870 incorporated within blood vessels may be able to also characterize and measure physical parameters of various types. For example, a blood vessel form of stent sensor 1870 may be able to measure pressures within the vessel during heart pumping cycles for a physiologically relevant determination of blood vessel pressure. There may be numerous manners that such a pressure sensor could function with small piezoelectric sensors, elastomeric sensors and other such sensors. There may be numerous physical parameters in addition to pressure that may be monitored directly within the blood stream.

A pill form biometric sensor, such as a swallowable pill 1880 may be used to provide biometric feedback. In some examples, the swallowable pill may incorporate pharmaceutical components. In other examples, the swallowable pill 1880 may simply contain biometric sensors of various kinds. The swallowable pill 1880 may perform analyte measurements of the gastrointestinal fluids that it incorporates. Furthermore, the pills may provide central core temperature measurements as a non-limiting example of physical measurements that may be performed. The rate of movement of the pill through the user's digestive track may also provide additional information of biometric relevance. In some examples, analyte sensors may be able to provide measurements related to dietary consumption and nutritional aspects.

A bandage form biometric sensor 1890 may be used to perform biometric sensing. In some examples, the bandage form biometric sensor 1890 may be similar to a wearable sensor 1850 and perform measurements upon chemicals in the skin environment including aspects of perspiration. The bandage form biometric sensor 1890 may also perform physical measurements. In some special examples, the bandage may be in the proximity of a wound of various kinds of the user, and the chemical and physical measurements in the region may have a specialized purpose relating to healing. In other examples, the bandage sensor may be a useful form factor or environmentally controlled region for the inclusion of a biometric sensor.

A biometric sensor may be incorporated within a neural implant 1895. A neural implant may be made into the brain of a user in some examples where it may have an active or passive role. Biometric sensors incorporated with the neural implant may allow for chemical and physical monitoring in addition to electrical and electrochemical type measurements that may be unique to neural related implants. A neural implant may in fact be placed in numerous locations within a user's body in conjunction with nerve systems and the biometric sensing role may enhance capabilities. In some examples, a neural implant may be used to sense an electrical impulse at a nerve and in so doing provide a user a control aspect for aspects of the biometric information communication systems described herein. In an alternative sense, neural related implants may also provide additional means for a biometric information communication system to provide information to the user as a feedback element.

The biometric sensor types depicted in FIG. 18 may represent exemplary types of sensors that may be consistent with the present invention. There may be numerous other types of sensors that may be consistent with the present invention however. Furthermore, there may be examples of sensors that combine some or all the functional aspects discussed in relation to FIG. 18 which may be relevant. The present invention is not meant to be limited to those examples provided in FIG. 18.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for communicating a targeted and individualized message comprising:
obtaining a first device, wherein the first device is capable to measure at least a first biometric of a user;
measuring the first biometric with the first device to obtain biometric data;
obtaining a second device, wherein the second device includes a display and a network communication device;
authorizing a paired communication between the first device and the second device;
communicating the biometric data from the first device to the second device;
determining a location of the first device with the second device to obtain location data;
communicating the biometric data and the location data to a computing device connected to a network;
authorizing the computing device, via a signal from the first device, to obtain behavioral information and environmental data related to the location data;
authorizing the computing device to Initiate an algorithm to be executed to retrieve a targeted and individualized content based on the biometric data, the behavioral information, the environmental data, the location data and an individualized preference determination calculated via predictive analysis to generate the targeted and individualized content;
receiving a message comprising the targeted and individualized content to the second device; and
displaying the message to the user.

2. The method according to claim 1, wherein the first device comprises a worn biomedical device.

3. The method according to claim 2, wherein the worn biomedical device is a contact lens.

4. The method according to claim 2, wherein the worn biomedical device is a smart ring.

5. The method according to claim 2, wherein the second device comprises a smart phone.

6. The method according to claim 2, wherein the second device comprises a smart watch.

7. The method according to claim 2, wherein the first device comprises a sub-cutaneous biomedical device.

8. The method according to claim 1, wherein the targeted and individualized content comprises at least one of an advertisement or promotional content.

* * * * *